United States Patent
Priceman et al.

(10) Patent No.: US 12,281,152 B2
(45) Date of Patent: Apr. 22, 2025

(54) TAG72 TARGETED CHIMERIC ANTIGEN RECEPTOR MODIFIED T CELLS FOR TREATMENT OF TAG72-POSITIVE TUMORS

(71) Applicant: City of Hope, Duarte, CA (US)

(72) Inventors: Saul J. Priceman, Valley Village, CA (US); John P. Murad, Diamond Bar, CA (US); Stephen J. Forman, Duarte, CA (US); John (Jack) E. Shively, Duarte, CA (US); Paul Yazaki, Duarte, CA (US); David Colcher, Duarte, CA (US); Anna Kozlowska, Duarte, CA (US); Hee Jun Lee, Diamond Bar, CA (US)

(73) Assignee: City of Hope, Duarte, CA (US)

( * ) Notice: Subject to any disclaimer, the term of this patent is extended or adjusted under 35 U.S.C. 154(b) by 934 days.

(21) Appl. No.: 17/264,911

(22) PCT Filed: Aug. 1, 2019

(86) PCT No.: PCT/US2019/044751
§ 371 (c)(1),
(2) Date: Feb. 1, 2021

(87) PCT Pub. No.: WO2020/028721
PCT Pub. Date: Feb. 6, 2020

(65) Prior Publication Data
US 2021/0308184 A1 Oct. 7, 2021

Related U.S. Application Data

(60) Provisional application No. 62/713,485, filed on Aug. 1, 2018.

(51) Int. Cl.
| | | |
|---|---|---|
| C12N 15/62 | (2006.01) | |
| A61K 35/17 | (2015.01) | |
| A61K 39/00 | (2006.01) | |
| A61P 35/00 | (2006.01) | |
| C07K 14/705 | (2006.01) | |
| C07K 14/715 | (2006.01) | |
| C07K 14/725 | (2006.01) | |
| C07K 14/73 | (2006.01) | |
| C07K 16/30 | (2006.01) | |
| C12N 5/0783 | (2010.01) | |
| C12N 5/10 | (2006.01) | |

(52) U.S. Cl.
CPC ...... *C07K 14/7051* (2013.01); *A61K 39/4611* (2023.05); *A61K 39/4631* (2023.05); *A61K 39/464469* (2023.05); *A61K 39/46447* (2023.05); *A61P 35/00* (2018.01); *C07K 14/70514* (2013.01); *C07K 14/70521* (2013.01); *C07K 14/7151* (2013.01); *C07K 16/3092* (2013.01); *C12N 5/0636* (2013.01); *A61K 2239/31* (2023.05); *A61K 2239/59* (2023.05); *C07K 2317/53* (2013.01); *C07K 2317/622* (2013.01); *C07K 2319/02* (2013.01); *C07K 2319/03* (2013.01); *C07K 2319/33* (2013.01); *C12N 2501/20* (2013.01)

(58) Field of Classification Search
None
See application file for complete search history.

(56) References Cited

U.S. PATENT DOCUMENTS

| | | |
|---|---|---|
| 6,818,749 B1 | 11/2004 | Kashmiri et al. |
| 7,319,139 B2 | 1/2008 | Braslawsky et al. |
| 7,700,097 B2 | 4/2010 | Braslawsky et al. |
| 11,730,797 B2 | 8/2023 | Wang et al. |
| 2009/0041758 A1* | 2/2009 | Glaser ............... A61P 7/04 |
| | | 435/325 |

FOREIGN PATENT DOCUMENTS

| | | |
|---|---|---|
| CN | 108136014 | 6/2018 |
| JP | 2007-535296 | 12/2007 |
| JP | 2017-537627 | 12/2017 |
| WO | WO 1989/000692 | 1/1989 |
| WO | WO 2004/003155 | 1/2004 |
| WO | WO 2005/000899 | 1/2005 |
| WO | WO 2005/021594 | 3/2005 |
| WO | WO 2017/040529 | 3/2017 |
| WO | WO 2017/088012 | 6/2017 |

OTHER PUBLICATIONS

Mizraei et al, Chimeric Antigen Receptors T Cell Therapy in Solid Tumor: Challenges and Clinical Applications, Front, Immunl, 2017, pp. 1-13.*
Newick et al, Chimeric Antigen Receptors T Cell Therapy for Solid Tumor, Molecular Therapy-Oncolytics, 22016, pp. 1-7.*
Shanks et al, Philosophy, Ethics, and Humanities in Medicine 2009, pp. 1-20.*
Jun Lee et al., Antigen-dependent IL-12 signaling in CAR T cells promotes regional to systemic disease targeting, Nature Communications, (2023) pp. 1-16.*
Anastasi et al., "The use of HE4, CA125 and CA72-4 biomarkers for differential diagnosis between ovarian endometrioma and epithelial ovarian cancer," Journal of Ovarian Research, 2013, 6(1):44.
Blidner et al., "Driving CARs into Sweet Roads: Targeting Glycosylated Antigens in Cancer," Immunity, Jun. 21, 2016, 4(6):1248-1250.
Castellarin et al., "Driving cars to the clinic for solid tumors," Gene therapy, Jun. 7, 2018, 25:165-175.

(Continued)

*Primary Examiner* — Maria Marvich
(74) *Attorney, Agent, or Firm* — Fish & Richardson P.C.

(57) ABSTRACT

Chimeric antigen receptors targeted to TAG72 and the use thereof to treat ovarian cancer and other cancers are described.

42 Claims, 17 Drawing Sheets
Specification includes a Sequence Listing.

(56) References Cited

OTHER PUBLICATIONS

Chauhan et al., "Combined staining of TAG-72, MUC1, and CA125 improves labeling sensitivity in ovarian cancer: antigens for multi-targeted antibody-guided therapy," The Journal of Histochemistry and Cytochemistry: Official Journal of the Histochemistry Society, Aug. 1, 2007, 55(8):867-875.

Chen et al., "Driving CARs on the uneven road of antigen heterogeneity in solid tumors," Current opinion in immunology, Apr. 2018, 51:103-110.

Cheng, "Radioiodinated anti-TAG72 CC49 Fab' antibody fragment," Molecular Imaging and Contrast Agent Database (MICAD), Mar. 10, 2008, 6 pages.

De Pascalis et al., "In vitro affinity maturation of a specificity-determining region-grafted humanized anticarcinoma antibody: isolation and characterization of minimally immunogenic high-affinity variants," Clinical cancer research., Nov. 15, 2003, 9(15):5521-5531.

Gonzales et al., "Minimizing immunogenicity of the SDR-grafted humanized antibody CC49 by genetic manipulation of the framework residues," Molecular immunology., 2003, 40(6):337-349.

Hand et al., "Influence of spatial configuration of carcinoma cell populations on the expression of a tumor-associated glycoprotein," Cancer research, Feb. 1985; 45(2):833-840.

Hege et al., "Safety, tumor trafficking and immunogenicity of chimeric antigen receptor (CAR)-T cells specific for TAG72 in colorectal cancer," Journal for immunotherapy of cancer, 2017, 5(1):22.

Hollingsworth et al., "Mucins in cancer: protection and control of the cell surface," Nature Reviews Cancer, 2004, 4(1):45-60.

International Search Report in International Application No. PCT/US2019/044751, dated Nov. 4, 2019, 19 pages.

Jain et al., "Concise Review: Emerging Principles from the Clinical Application of Chimeric Antigen Receptor T Cell Therapies for B Cell Malignancies," Stem cells, 2018, 36(1):36-44.

Jensen et al., "Design and implementation of adoptive therapy with chimeric antigen receptor-modified T cells," Immunological Reviews, Dec. 13, 2013, 257(1):127-144.

Jonnalagadda et al., "Chimeric antigen receptors with mutated IgG4 Fc spacer avoid fc receptor binding and improve T cell persistence and antitumor efficacy," Mol Ther., Apr. 2015, 23(4):757-768.

Julien et al., "Sialyl-tn in cancer: (how) did we miss the target?" Biomolecules, 2012, 2(4):435-466.

Kashmiri et al., "Generation, characterization, and in vivo studies of humanized anticarcinoma antibody CC49," Hybridoma, 1995, 14(5):461-473.

Maude et al., "CD 19-targeted chimeric antigen receptor T-cell therapy for acute lymphoblastic leukemia," Blood, 2015, 125(26):4017-4023.

Murad et al., "Effective Targeting of TAG72+ Peritoneal Ovarian Tumors via Regional Delivery of CAR-Engineered T Cells," Front Immunol., Nov. 2018, 9:2268.

Muraro et al., "Generation and characterization of B72.3 second generation monoclonal antibodies reactive with the tumor-associated glycoprotein 72 antigen," Cancer Research, 1988, 48(16):4588-4596.

Pavlinkova et al., "Effects of humanization and gene shuffling on immunogenicity and antigen binding of anti-TAG72 single-chain Fvs," International journal of cancer., Oct. 30, 2001, 94(5):717-726.

Pavlinkova et al., "Radioimmunotherapy of human colon cancer xenografts using a dimeric single-chain Fv antibody construct," Clinical Cancer Research, 1999, 5(9):2613-2619.

Ponnusamy et al., "Expression of TAG-72 in ovarian cancer and its correlation with tumor stage and patient prognosis," Cancer letters, 2007, 251(2):247-257.

Posey et al., "Engineered CAR T Cells Targeting the Cancer-Associated Tn-Glycoform of the Membrane Mucin MUC1 Control Adenocarcinoma," Immunity, Jun. 21, 2016, 44(6):1444-1454.

Priceman et al., "Co-stimulatory signaling determines tumor antigen sensitivity and persistence of CART cells targeting PSCA+ metastatic prostate cancer," Oncoimmunology, 2018, 7(2):e1380764.

Priceman et al., "Regional delivery of chimeric antigen receptor-engineered T cells effectively targets HER2(+) breast cancer metastasis to the brain," Clin Cancer Res., 2018, 24:95-105.

Priceman et al., "Smart CARs engineered for cancer immunotherapy," Current opinion in oncology, 2015, 27(6):466-474.

Rodriguez et al., "The tumour glyco-code as a novel immune checkpoint for immunotherapy," Nature reviews Immunology., 2018, 18(3):204-211.

Sharifzadeh et al., "Genetically engineered T cells bearing chimeric nanoconstructed receptors harboring TAG-72-specific camelid single domain antibodies as targeting agents," Cancer Letters, 2013, 334:237-244.

Steentoft et al., "Glycan-Directed Car-T Cells," Glycobiology, Sep. 2018, 28(9):656-669.

Van Der Stegen et al., "The pharmacology of second-generation chimeric antigen receptors," Nature Reviews Drug Discovery, 2015, 14:499-509.

Wang et al., "Clinical value of serum tumor markers CA19-9, CA125 and CA72-4 in the diagnosis of pancreatic carcinoma," Molecular and Clinical Oncology, 2014, 2(2):265-268.

Yong et al., CAR T-cell therapy of solid tumors. Immunology and cell biology. 2017;9 5(4):356-363.

Zhao et al., "Structural Design of Engineered Costimulation Determines Tumor Rejection Kinetics and Persistence of CAR T Cells," Cancer Cell, Oct. 12, 2015, 28(4):415-428.

Zheng et al., "Protein L: a novel reagent for the detection of chimeric antigen receptor (CAR) expression by flow cytometry," J Transl Med., 2012, 10:29.

Zou et al., "Near-infrared fluorescence labeled anti-TAG-72 monoclonal antibodies for tumor imaging in colorectal cancer xenograft mice," Mol Pharm., Mar.-Apr. 2009, 6(2):428-440.

* cited by examiner

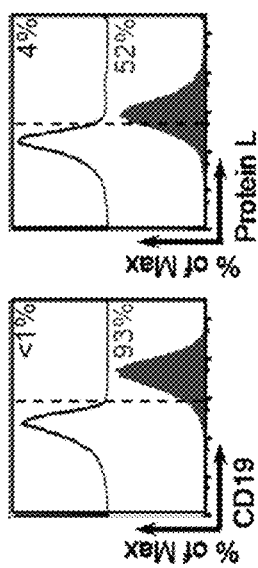
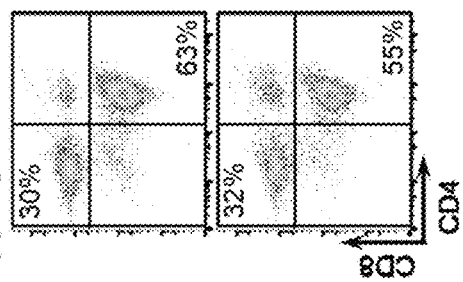
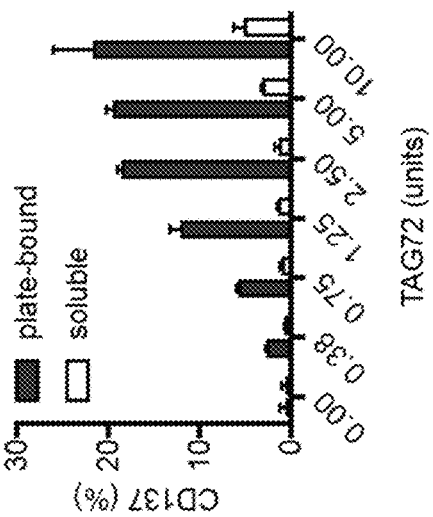
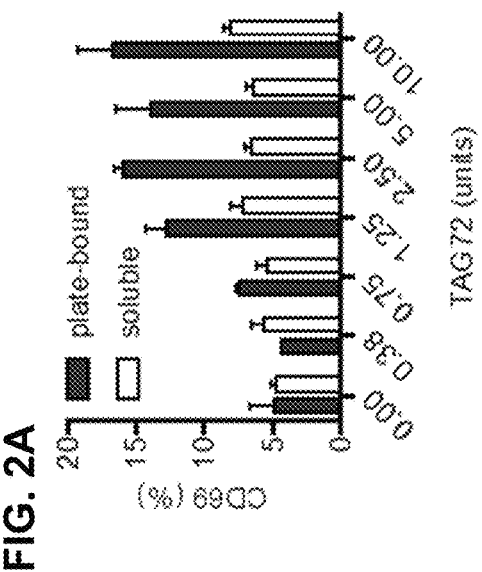
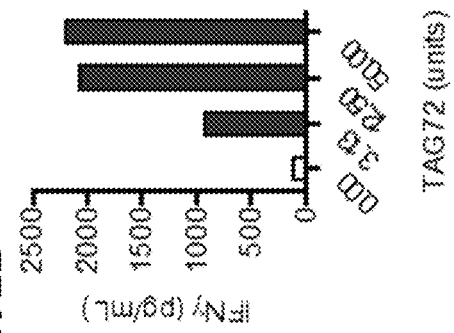

FIG. 3A
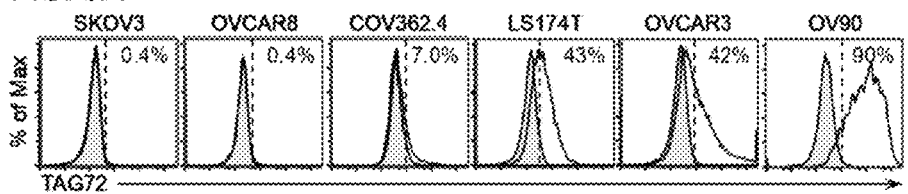
FIG. 3B
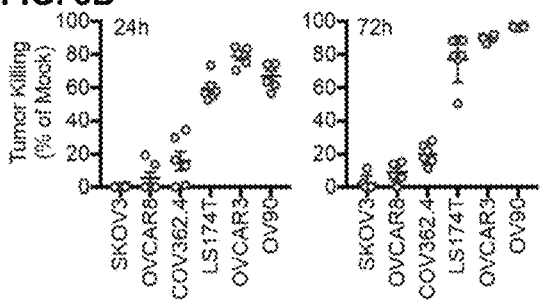
FIG. 3C
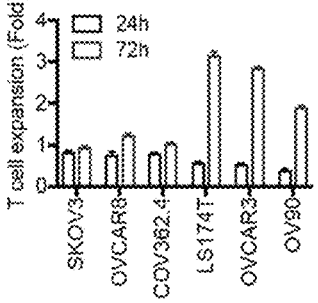
FIG. 3D
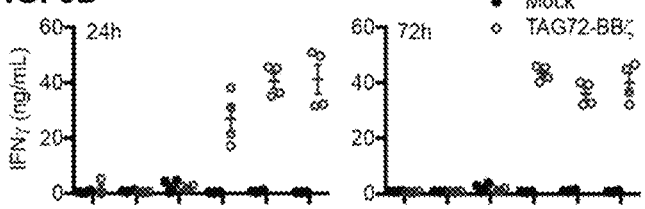
FIG. 3F
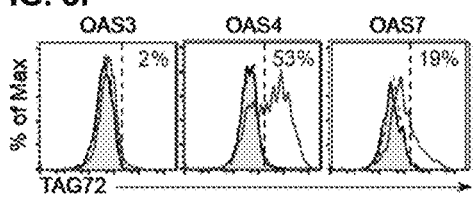
FIG. 3E
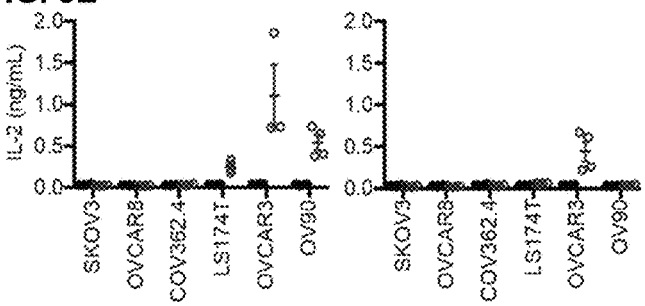
FIG. 3G
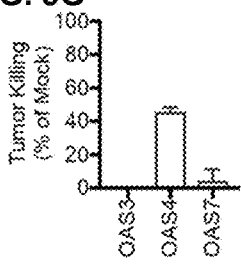
FIG. 3H
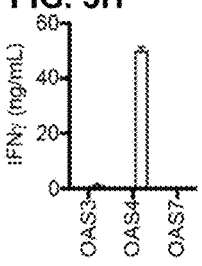
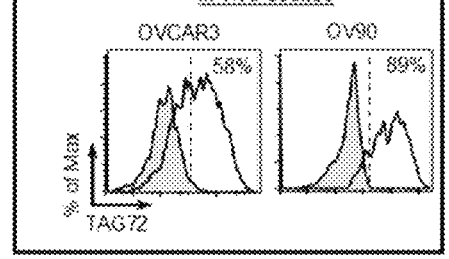
FIG. 4
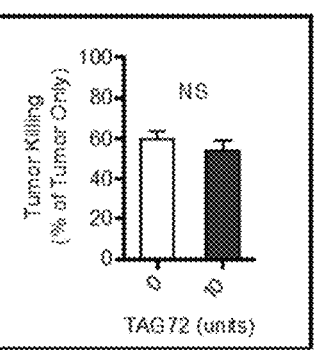
FIG. 5

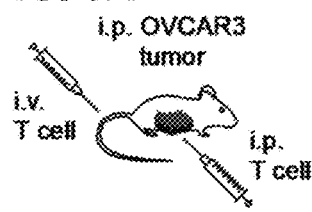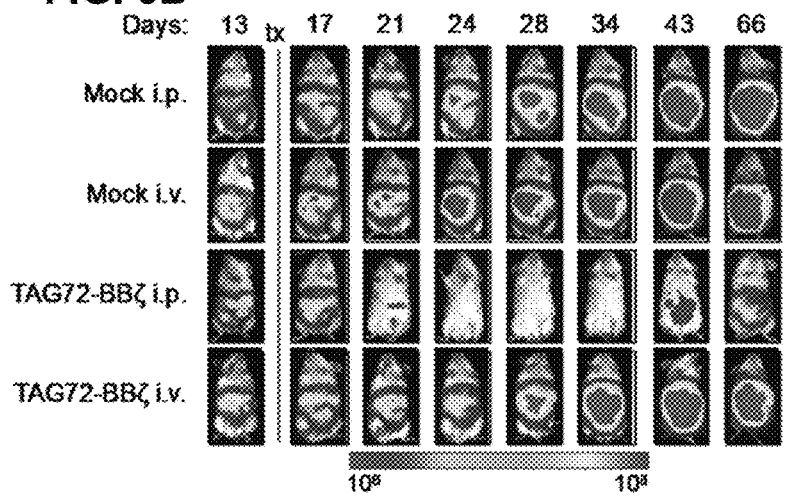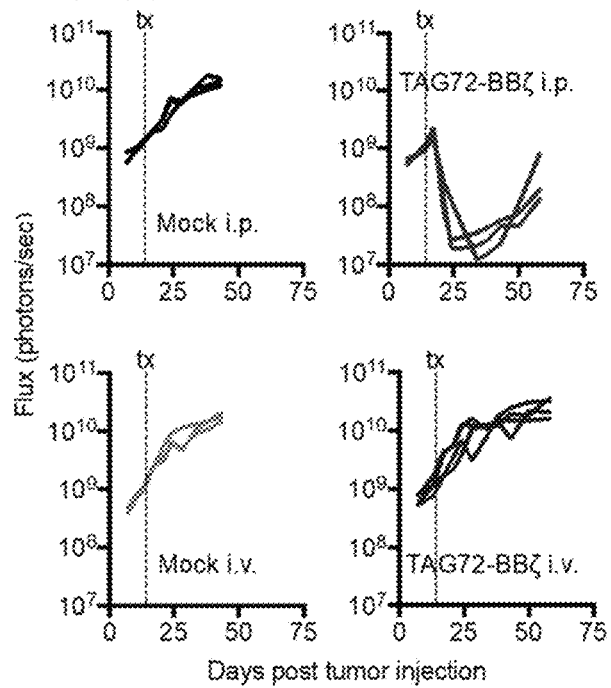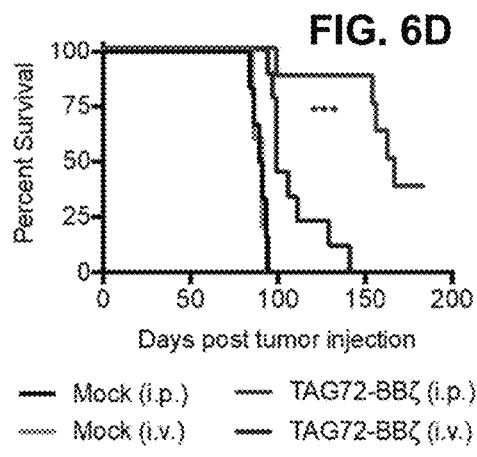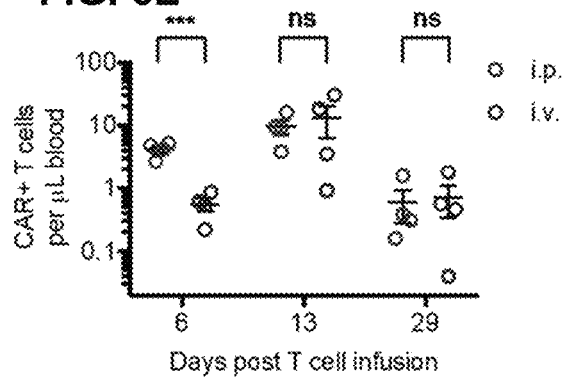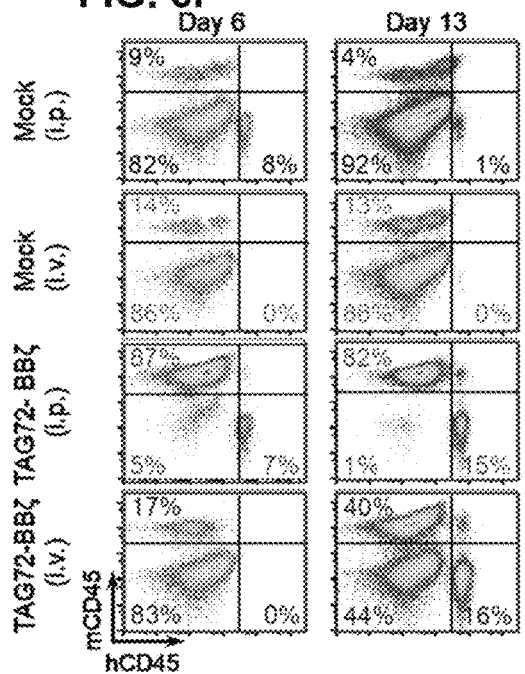

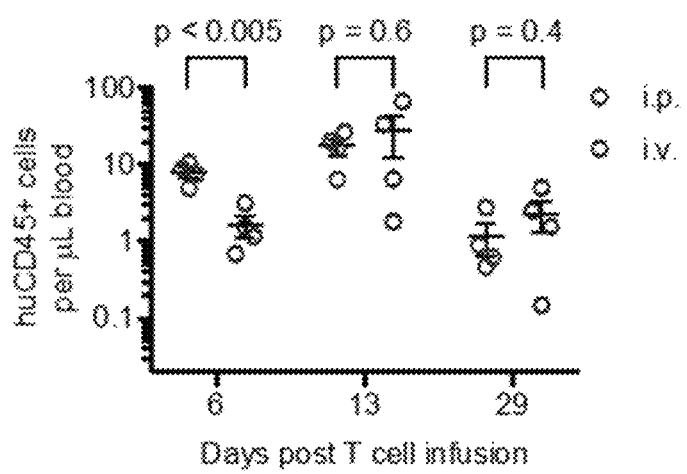
FIG. 7
FIG. 8A
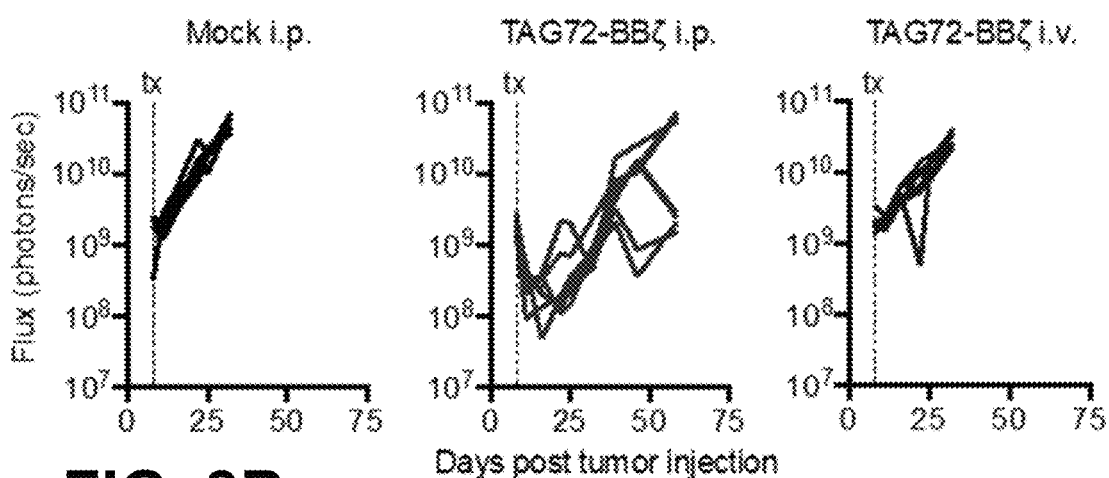
FIG. 8B
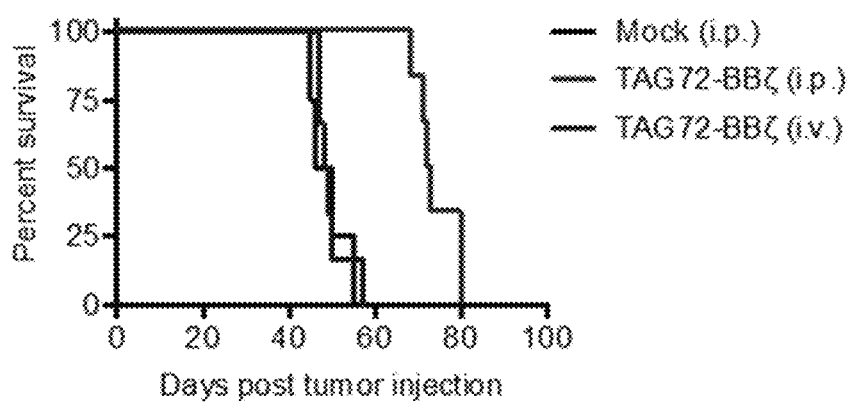

FIG. 9A
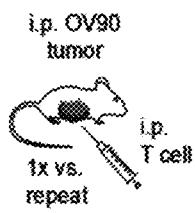
FIG. 9B
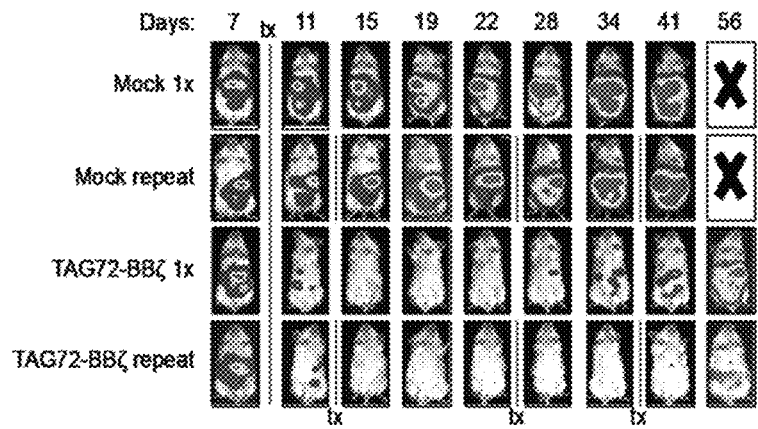
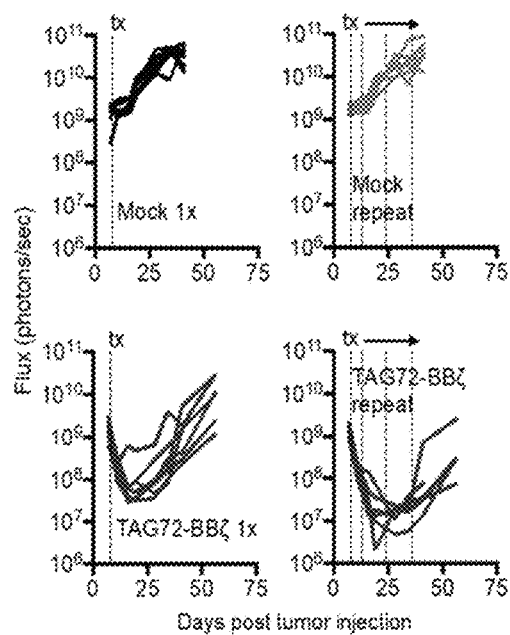
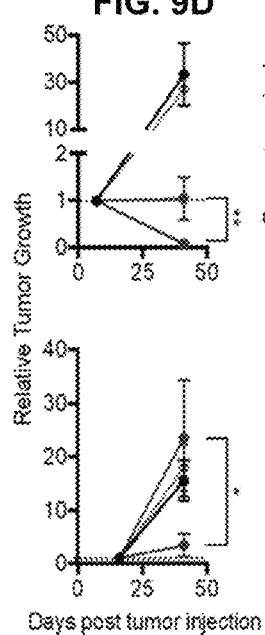
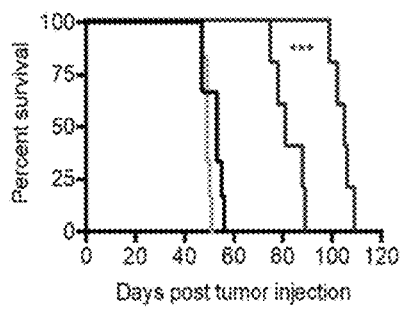
FIG. 9F
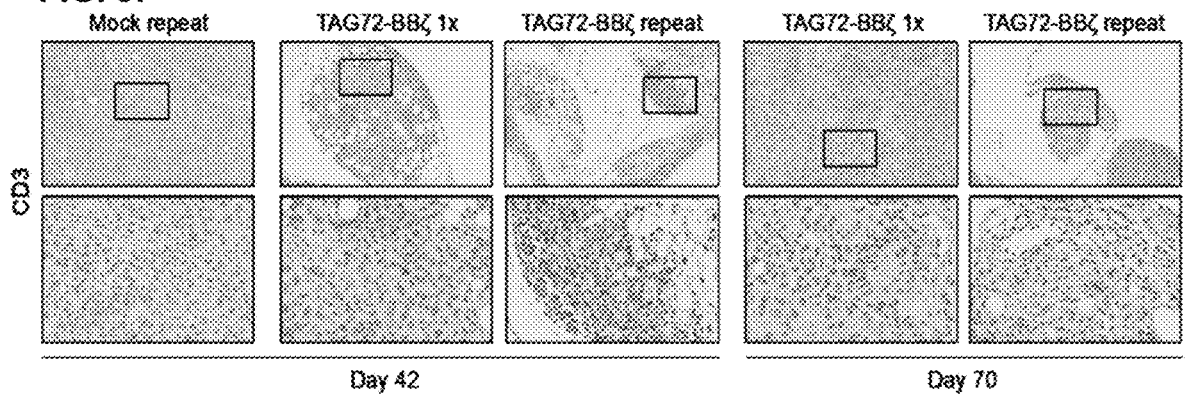

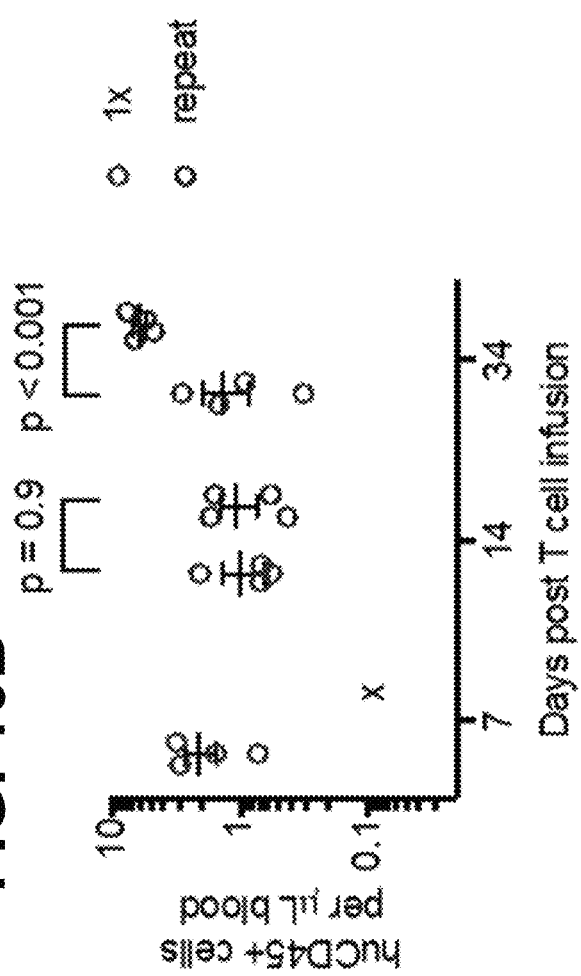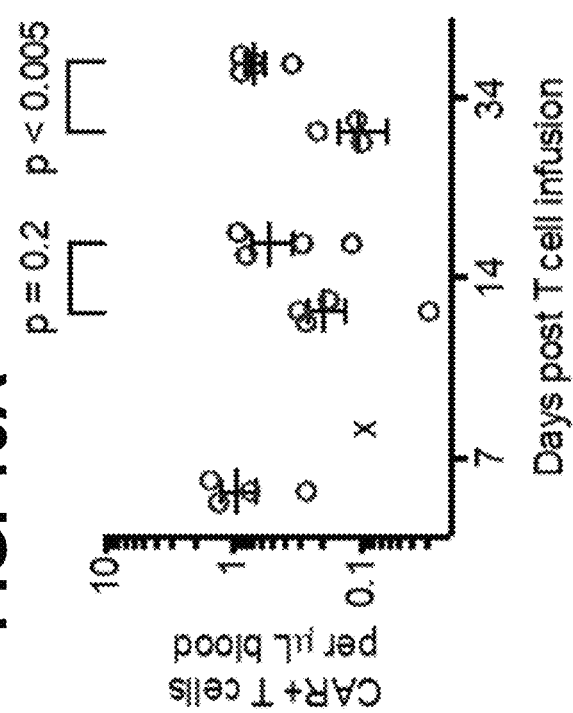
FIG. 10A
FIG. 10B

MLLLVTSLLLCELPHPAFLLIPQVQLVQSGAEVKKPGASVKISCKASGYTFTDHAIHWVKQNPG
QRLEWIGYFSPGNDDFKYNERFKGKATLTADTSASTAYVELSSLRSEDTAVYFCTRSLNMAYWG
QGTLVTVSSGSTSGSGGSGGGSSGGGSSDIVMSQSPDSLAVSLGERVTLNCKSSQSLLYSGNQRN
YLAWYQQKPGQSPKLLIYWASARESGVPDRFSGSGSGTDFTLTISSVQAEDVAVYYCQQYYSYP
LTFGAGTKLELKESKYGPPCPPCPGGGSSGGGSGGQPREPQVYTLPPSQEEMTKNQVSLTCLVK
GFYPSDIAVEWESNGQPENNYKTTPPVLDSDGSFFLYSRLTVDKSRWQEGNVFSCSVMHEALHN
HYTQKSLSLSLGKMALIVLGGVAGLLLFIGLGIFFRRGRKKLLYIFKQPFMRPVQTTQEEDGCS
CRFPEEEEGGCELGGGRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQALPPR
LEGGGEGRGSLLTCGDVEENPGPRMPPPRLLFFLLFLTPMEVRPEEPLVVKVEEGDNAVLQCLK
GTSDGPTQQLTWSRESPLKPFLKLSLGLPGLGIHMRPLAIWLFIFNVSQQMGGFYLCQPGPPSE
KAWQPGWTVNVEGSGELFRWNVSDLGGLGCGLKNRSSEGPSSPSGKLMSPKLYVWAKDRPEIWE
GEPPCVPPDSLNQSLSQDLTMAPGSTLWLSCGVPPDSVSRGPLSWTHVHPKGPKSLLSLELKD
DRPARDMWVMETGLLLPRATAQDAGKYYCHRGNLTMSFHLEITTARPVLMHWLLRTGGWKVSAVT
LAYLIFCLCSLVGILHLQRALVLRRKR

Legend:
GMCSFRa signal peptide
Taq72 scFv
IgG4 Hinge with amino acid at position 10 mutated to proline (P)
linker
IgG4 CH3 domain
CD4 transmembrane domain
4-1BB co-stimulatory domain
CD3 zeta
T2A ribosomal skip sequence
CD19t

FIG. 12

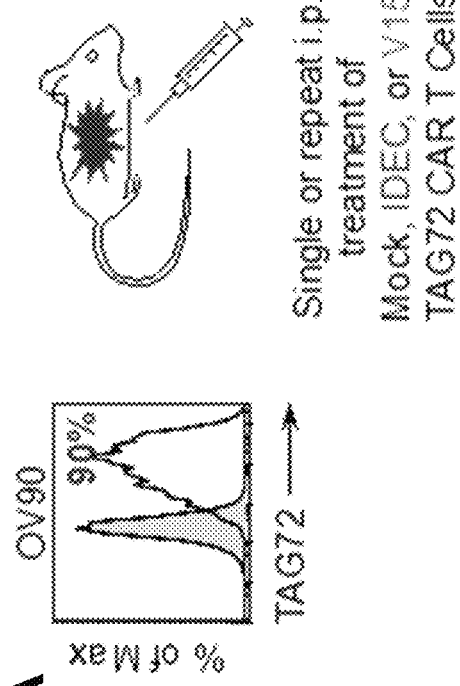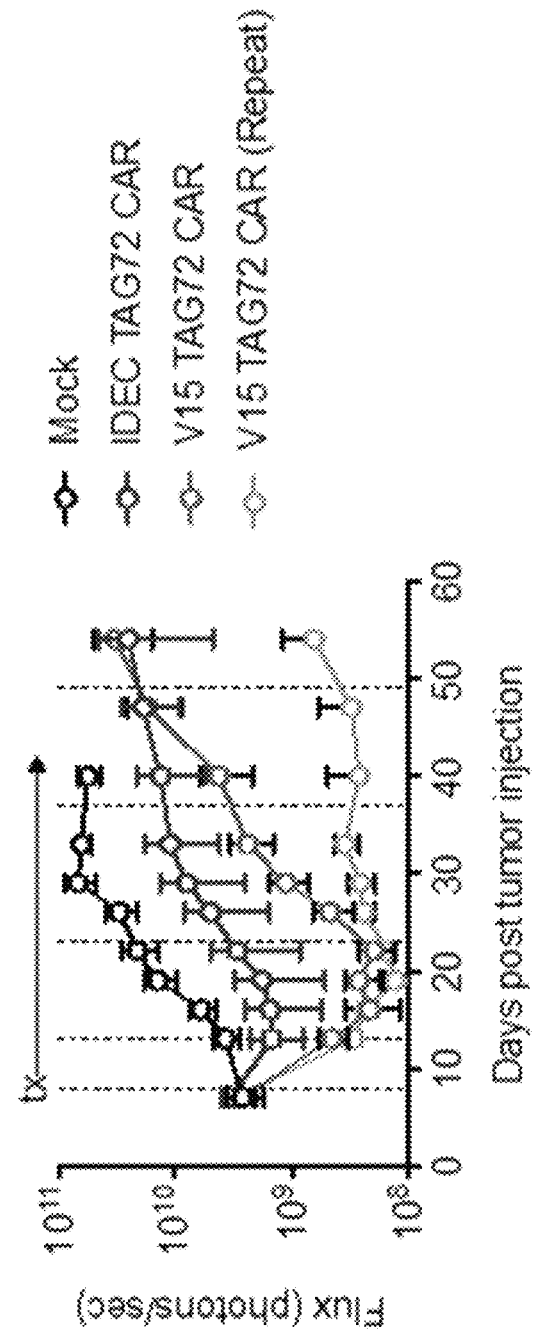
FIG. 14A
FIG. 14B

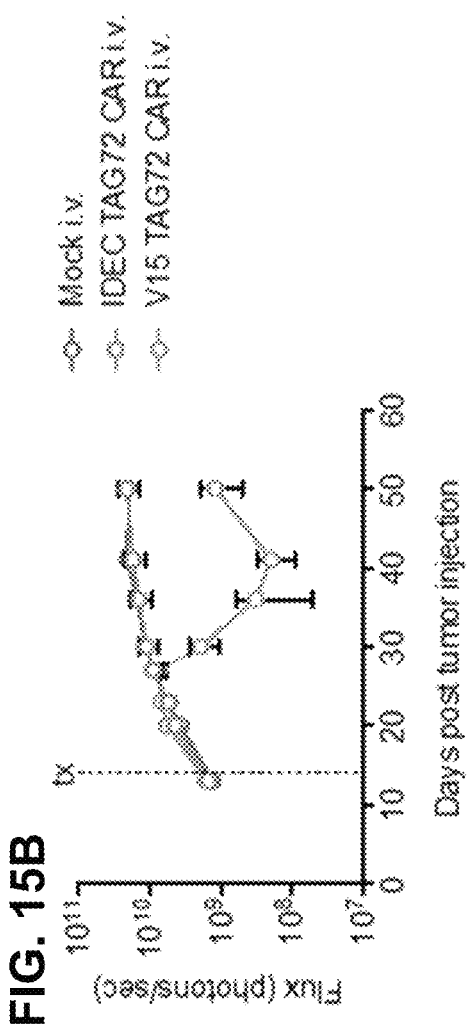
FIG. 15A
FIG. 15B
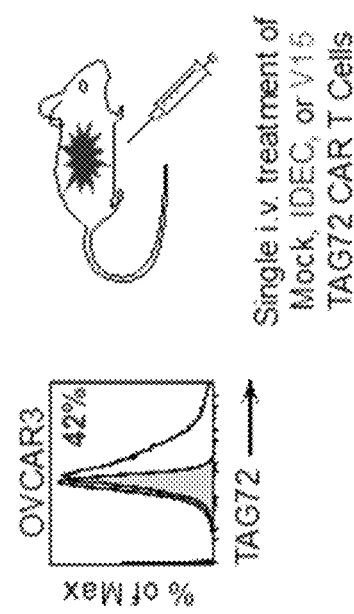
FIG. 15C
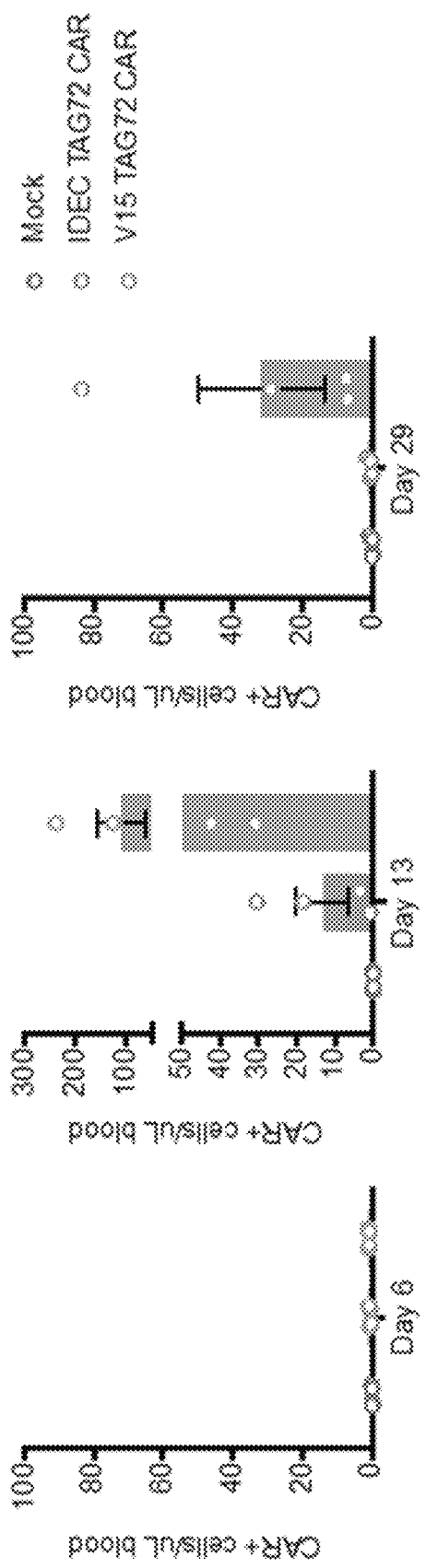

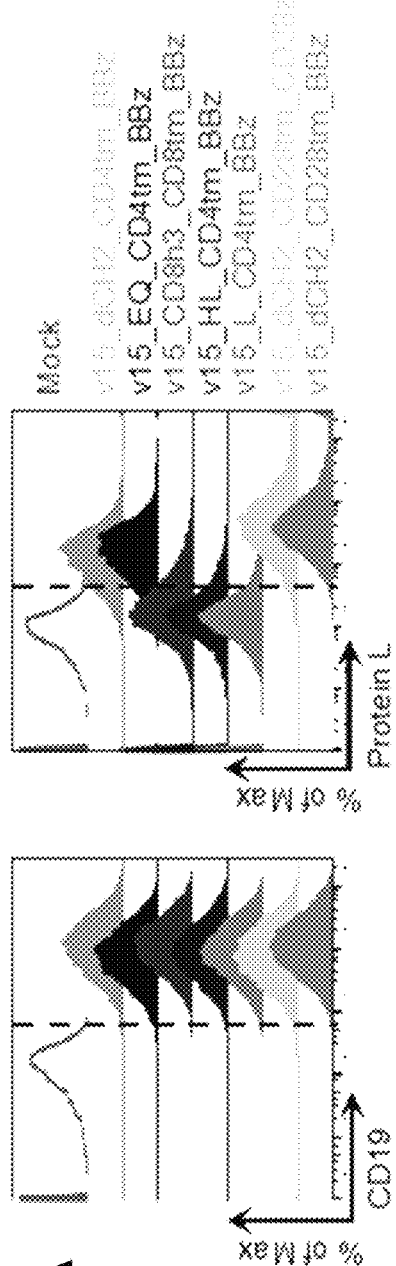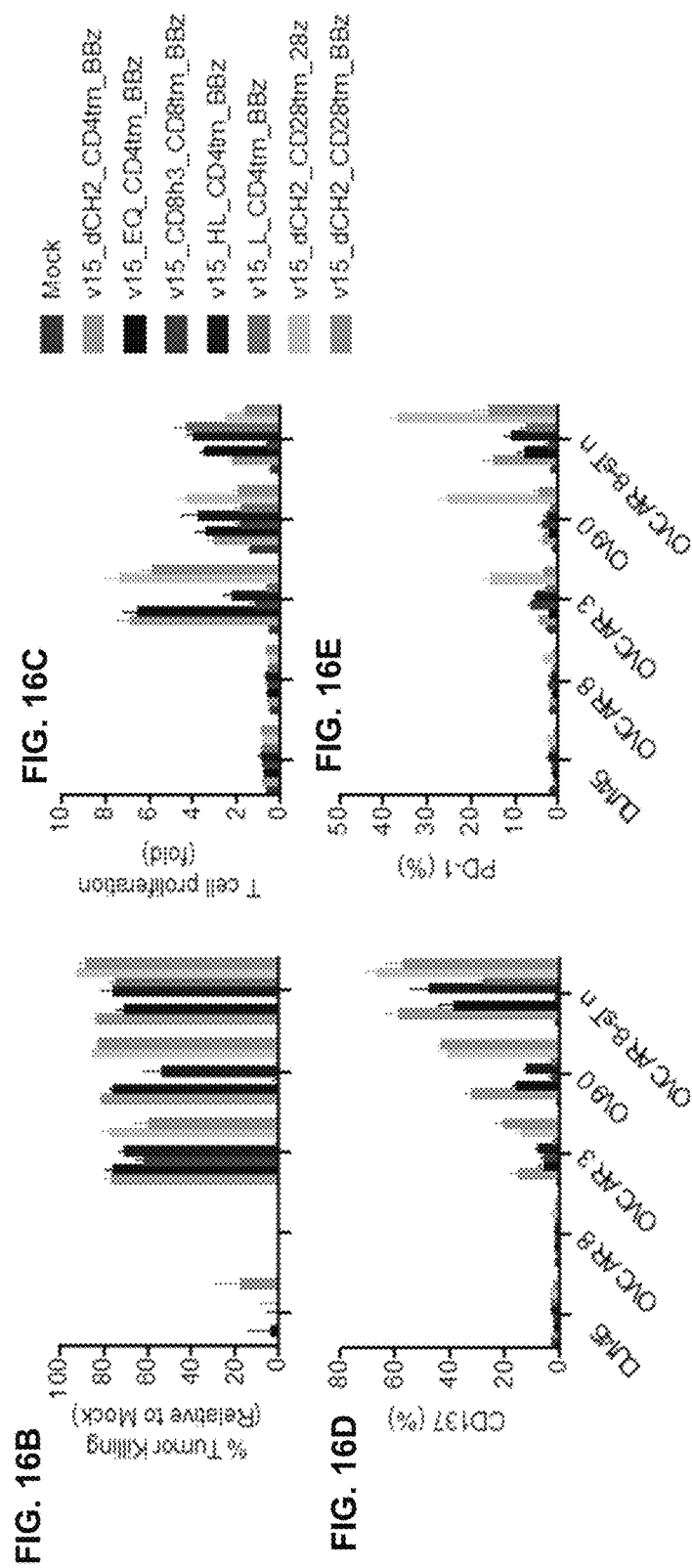
FIG. 16A
FIG. 16B
FIG. 16C
FIG. 16D
FIG. 16E

Tag72scfv(IDEC)-IgG4(HL-CH3)-CD4tm-41BB-Zeta

MLLLVTSLLLCELPHPAFLLIPQVQLVQSGAEVVKPGASVKISCKASGYTFTDHAIHWVKQNP
<u>GMCSFRa signal peptide</u>    <u>Tag72scFv(IDEC)</u>

GQRLEWIGYFSPGNDDFKYNERFKGKATLTADTSASTAYVELSSLRSEDTAVYFCTRSLNMA
YWGQGTLVTVSSGSTSGGGSGGGGSSDIVMSQSPDSLAVSLGERVTLNCKSSQSLLY
SGNQKNYLAWYQQKPGQSPKLLIYWASARESGVPDRFSGSGSGTDFTLTISSVQAEDVAVY
YCQQYYSYPLTFGAGTKLELKESKYGPPCPPCPGGSSGGGGSGGGGSGGGGSQPREPQVYTLPPSQEEMT
                                            <u>IgG4Hinge</u>    <u>Linker</u>    <u>IgG4 CH3</u>

KNQVSLTCLVKGFYPSDIAVEWESNGQPENNYKTTPPVLDSDGSFFLYSRLTVDKSRWQEG
NVFSCSVMHEALHNHYTQKSLSLSLGKMALIVLGGVAGLLLFIGLGIFFKRGRKKLLYIFKQPF
                                         <u>CD4 transmembrane</u>     <u>4-1BB cyto</u>

MRPVQTTQEEDGCSCRFPEEEEGGCELGGGRVKFSRSADAPAYQQGQNQLYNELNLGRRE
                                   <u>Zeta</u>

EYDVLDKRRGRDPEMGGKPRRKNPQEGLYNELQKDKMAEAYSEIGMKGERRRGKGHDGL
YQGLSTATKDTYDALHMQALPPR

FIG. 19

Tag72scFv(v15)-IgG4(HL-CH3)-CD4tm-41BB-Zeta

MLLLVTSLLLCELPHPAFLLIPQVQLVQSGAEVVKPGASVKISCKASGYTFTDHAIHWVKQNP
<u>GMCSFRa signal peptide</u> <u>Tag72scFv(v15)</u>

GQRLEWIGYFSPGNDDFKYSQKFQGKATLTADTSASTAYVELSSLRSEDTAVYFCTRSLNMA
YWGQGTLVTVSSGSTSGGGSGGGSGGGSSDIVMSQSPDSLAVSLGERVTLNCKSSQSVLY
SSNSKNYLAWYQQKPGQSPKLLIYWASTRESGVPDRFSGSGSGTDFTLTISSVQAEDVAVYY
CQQYYSYPLSFGAGTKLELKESKYGPPCPPCPGGSSGGGSGGQPREPQVYTLPPSQEEMT
<u>IgG4Hinge</u> <u>Linker</u> <u>IgG4 CH3</u>

KNQVSLTCLVKGFYPSDIAVEWESNGQPENNYKTTPPVLDSDGSFFLYSRLTVDKSRWQEG
NVFSCSVMHEALHNHYTQKSLSLSLGKMALIVLGGVAGLLLFIGLGIFFKRGRKKLLYIFKQPF
<u>CD4 transmembrane</u> <u>4-1BB cyto</u>

MRPVQTTQEEDGCSCRFPEEEEGGCELGGGRVKFSRSADAPAYQQGQNQLYNELNLGRRE
<u>Zeta</u>

EYDVLDKRRGRDPEMGGKPRRKNPQEGLYNELQKDKMAEAYSEIGMKGERRRGKGHDGL
YQGLSTATKDTYDALHMQALPPR

FIG. 20

Tag72scFv(v59_v15)-IgG4(HL-CH3)-CD4tm-41BB-Zeta-T2A-CD19t

MLLLVTSLLLCELPHPAFLLIPQVQLVQSGAEVKKPGASVKVSCKASGYTFTDHAIHWVRQAP
<u>GMCSFRa signal peptide</u> <u>Tag72scFv(v59_v15)</u>

GQRLEWMGYFSPGNDDFKYSQKFQGRVTITADTSASTAYMELSSLRSEDTAVYFCTRSLNM
AYWGQGTLVTVSSGSTSGGGSGGGSGGGSDIVMTQSPDSLAVSLGERATINCKSSQSLL
YSSNSKNYLAWYQQKPGQPPKLLIYWASTRESGVPDRFSGSGSGTDFTLTISSLQAEDVAVY
YCQQPYSYPLSFGAGTKLELKESKYGPPCPPCPGGGSSGGGSGGGGSGGGGSGGGGSQPREPQVYTLPPSQEEMT
<u>IgG4Hinge</u>    <u>Linker</u>    <u>IgG4 CH3</u>

KNQVSLTCLVKGFYPSDIAVEWESNGQPENNYKTTPPVLDSDGSFFLYSRLTVDKSRWQEG
NVFSCSVMHEALHNHYTQKSLSLSLGKMALIVLGGVAGLLLFIGLGIFFKRGRKKLLYIFKQPF
                                <u>CD4 transmembrane</u>    <u>4-1BB cyto</u>

MRPVQTTQEEDGCSCRFPEEEEGGCELGGGRVKFSRSADAPAYQQGQNQLYNELNLGRRE
                                                                          <u>Zeta</u>

EYDVLDKRRGRDPEMGGKPRRKNPQEGLYNELQKDKMAEAYSEIGMKGERRRGKGHDGL
YQGLSTATKDTYDALHMQALPPR

FIG. 21

TAG72 TARGETED CHIMERIC ANTIGEN RECEPTOR MODIFIED T CELLS FOR TREATMENT OF TAG72-POSITIVE TUMORS

CROSS-REFERENCE TO RELATED APPLICATIONS

This application is a U.S. National Phase Application under 35 U.S.C. § 371 of International Application No. PCT/US2019/044751, filed on Aug. 1, 2019, which claims priority to and the benefit of U.S. Provisional Application No. 62/713,485, filed on Aug. 1, 2018. The entire contents of the foregoing are incorporated herein by reference.

SEQUENCE LISTING

This application contains a Sequence Listing that has been submitted electronically in ASCII format and is hereby incorporated by reference in its entirety. Said ASCII copy, created on Feb. 1, 2021, is named SequenceListing.txt and is 72787 bytes in size.

TECHNICAL FIELD

This disclosure concerns tumor-associated glycoprotein 72 (TAG72)-specific chimeric antigen receptor (CAR)-engineered T cells, methods of formulating, and methods of use as anti-cancer agents selective against TAG72-positive cells.

BACKGROUND

Chimeric Antigen Receptor (CAR)-engineered T cell therapy in patients with CD19+ B-cell malignancies have demonstrated impressive clinical responses, which have recently resulted in two landmark FDA approvals for patients with leukemia and lymphoma (Maude S L, Teachey D T, Porter D L, Grupp S A. CD19-targeted chimeric antigen receptor T-cell therapy for acute lymphoblastic leukemia. Blood. 2015; 125 (26): 4017-23; Jain M D, Davila M L. Concise Review: Emerging Principles from the Clinical Application of Chimeric Antigen Receptor T Cell Therapies for B Cell Malignancies. Stem cells. 2018; 36 (1): 36-44). These studies have shown that CAR T cells can be optimized to induce durable and complete responses in cancer patients, even under conditions of highly refractory disease. Major obstacles in developing effective CAR T cell therapies for solid cancers is avoiding off-tumor on-target toxicity due to the lack of truly restricted tumor antigens, as well as achieving durable responses that are limited by T cell persistence and tumor trafficking (Priceman S J, Forman S J, Brown C E. Smart CARs engineered for cancer immunotherapy. Current opinion in oncology. 2015; 27 (6): 466-74; Chen N, Li X, Chintala N K, Tano Z E, Adusumilli P S. Driving CARs on the uneven road of antigen heterogeneity in solid tumors. Current opinion in immunology. 2018; 51:103-10). To date, the majority of tumor antigens for directing specificity of CAR T cells have targeted overexpressed proteins, including but not limited to mesothelin, PSMA, PSCA, HER2/neu, EGFR, and IL13Rα2 (Priceman S J, Forman S J, Brown C E. Smart CARs engineered for cancer immunotherapy. Current opinion in oncology. 2015; 27 (6): 466-74; Yong C S M, Dardalhon V, Devaud C, Taylor N, Darcy P K, Kershaw M H. CAR T-cell therapy of solid tumors. Immunology and cell biology. 2017; 9 5 (4): 356-63). While the field is still evolving, the clinical efficacy of CAR T cells targeting these proteins in solid tumors have been somewhat limited (Castellarin M, Watanabe K, June C H, Kloss C C, Posey A D, Jr. Driving cars to the clinic for solid tumors. Gene therapy. 2018. Epub 2018 Jun. 9), and identification of additional targets as well as addressing limited T cell durability continue to be outstanding problems limiting the success of CAR T cell therapies.

Aberrant glycosylation of cell surface proteins on tumors have long been implicated in tumor development, and have unique glycoprotein signatures that are attractive targets for immunotherapy, including CAR T cells (Steentoft C, Migliorini D, King T R, Mandel U, June C H, Posey A D, Jr. Glycan-Directed Car-T Cells. Glycobiology. 2018. Epub 2018 Jan. 26; Rodriguez E, Schetters S T T, van Kooyk Y. The tumour glyco-code as a novel immune checkpoint for immunotherapy. Nature reviews Immunology. 2018; 18 (3): 204-11. Epub 2018 Feb. 6). Multiple cancer types including colon, breast, pancreas, and ovarian, are known to overexpress glycoproteins, including the mucins MUC16 and MUC1, and tumor associated glycoprotein-72 (TAG72) (Hollingsworth M A, Swanson B J. Mucins in cancer: protection and control of the cell surface. Nature reviews Cancer. 2004; 4 (1): 45-60. Epub 2003 Dec. 19), that differentiate them from normal epithelia. TAG72 is a high molecular weight mucin with large amounts of O-glycosidic linkages to serine and threonine residues (Julien S, Videira P A, Delannoy P. Sialyl-tn in cancer: (how) did we miss the target? Biomolecules. 2012; 2 (4): 435-66. Epub 2012 Jan. 1). High expression of TAG72, MUC1, and MUC16 has been shown in ovarian cancer patient tissue samples, with nearly 100-percent of ovarian cancers identified with simultaneous staining of the three antigens (Chauhan S C, Vinayek N, Maher D M, Bell M C, Dunham K A, Koch M D, Lio Y, Jaggi M. Combined staining of TAG72, MUC1, and CA125 improves labeling sensitivity in ovarian cancer: antigens for multi-targeted antibody-guided therapy. The journal of histochemistry and cytochemistry. 2007; 55 (8): 867-75). Importantly, approximately 90-percent of epithelial ovarian cancers are TAG72 positive, indicating its abundance across multiple histological subtypes of ovarian cancer.

Several monoclonal antibodies specific to the tumor-associated sialyl Tn antigen (STn antigen) of TAG72 have been developed, including the well-studied clone CC49 (Muraro R, Kuroki M, Wunderlich D, Poole D J, Colcher D, Thor A, Greiner J W, Simpson J F, Molinolo A, Noguchi P, et al. Generation and characterization of B72.3 second generation monoclonal antibodies reactive with the tumor-associated glycoprotein 72 antigen. Cancer research. 1988; 48 (16): 4588-96). CC49 has been subsequently utilized in multiple pre-clinical and clinical investigations using diagnostic imaging and radiotherapy and also involved in multiple attempts of antibody humanization (Cheng K T. Radioiodinated anti-TAG72 CC49 Fab' antibody fragment. Molecular Imaging and Contrast Agent Database (MICAD). Bethesda MD2004; Pavlinkova G, Booth B J, Batra S K, Colcher D. Radioimmunotherapy of human colon cancer xenografts using a dimeric single-chain Fv antibody construct. Clinical cancer research: an official journal of the American Association for Cancer Research. 1999; 5 (9): 2613-9; Kashmiri S V, Shu L, Padlan E A, Milenic D E, Schlom J, Hand P H. Generation, characterization, and in vivo studies of humanized anticarcinoma antibody CC49. Hybridoma. 1995; 14 (5): 461-73; De Pascalis R, Gonzales N R, Padlan E A, Schuck P, Batra S K, Schlom J, Kashmiri S V. In vitro affinity maturation of a specificity-determining region-grafted humanized anticarcinoma antibody: isolation and characterization of minimally immunogenic high-affinity variants. Clinical cancer research: an official journal of the American Association for Cancer Research. 2003; 9 (15): 5521-31; Gonzales N R, Padlan E A, De Pascalis R, Schuck P, Schlom J, Kashmiri S V. Minimizing immunogenicity of the SDR-grafted humanized antibody CC49 by genetic manipulation of the framework residues. Molecular immunology. 2003; 40 (6): 337-49; Pavlinkova G, Colcher D, Booth B J, Goel A, Wittel U A, Batra S K. Effects of humanization and gene shuffling on immunogenicity and antigen binding of anti-TAG72 single-chain Fvs. International journal of cancer. 2001; 94 (5): 717-26; Hege K M, Bergsland E K, Fisher G A, Nemunaitis J J, Warren R S, McArthur J G, Lin A A, Schlom J, June C H, Sherwin S A. Safety, tumor trafficking and immunogenicity of chimeric antigen receptor (CAR)-T cells specific for TAG72 in colorectal cancer. Journal for immunotherapy of cancer. 2017; 5:22).

SUMMARY

Described herein are methods for using TAG72 targeted CAR T cells to treat a variety of cancers, for example, ovarian cancer.

Described herein is a nucleic acid molecule comprising a nucleotide sequence encoding a chimeric antigen receptor (CAR), wherein the chimeric antigen receptor comprises: an scFv targeting Tag-72, a spacer, a transmembrane domain, a 41-BB co-stimulatory domain or CD28 co-stimulatory domain, and a CD3 ζ signaling domain.

In various embodiments: the transmembrane domain is selected from: a CD4 transmembrane domain or variant thereof having 1-5 amino acid modifications, a CD8 transmembrane domain or variant thereof having 1-5 amino acid modifications, a CD28 transmembrane domain or a variant thereof having 1-5 amino acid modifications; the spacer comprises 20-150 amino acids and is located between the scFv and the transmembrane domain; the transmembrane domain is a CD4 transmembrane domain or variant thereof having 1-5 amino acid modifications; the transmembrane domain is a CD4 transmembrane domain; the chimeric antigen receptor comprises a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications; the spacer region comprises an amino acid sequence selected from the group consisting of SEQ ID NOs: 2-12 or a variant thereof having 1-5 amino acid modifications; the spacer comprises an IgG hinge region; the spacer comprises 10-50 amino acids; the 4-1BB costimulatory domain comprises the amino acid sequence of SEQ ID NO: 24 or a variant thereof having 1-5 amino acid modifications; the CD3 ζ signaling domain comprises the amino acid sequence of SEQ ID NO:21; a linker of 3 to 15 amino acids is located between the 4-1BB costimulatory domain and the CD3 ζ signaling domain or variant thereof; the CAR comprises the amino acid sequence of SEQ ID NO: 29 or a variant thereof having 1-5 amino acid modifications; the scFv comprises the amino acid sequence of SEQ ID NO:1, SEQ ID NO:33 or SEQ ID NO:34.

Also disclosed herein is: a viral vector comprising a nucleic acid molecule described herein; a population of human T cells (e.g., a population comprising central memory T cells) transduced by a vector comprising a nucleic acid molecule described herein.

Also described herein is a method of treating solid tumor in a patient comprising administering a population of autologous or allogeneic human T cells transduced by a vector comprising a nucleic acid molecule described herein, wherein the solid tumor comprises cells expressing Tag-72. In various embodiments: the chimeric antigen receptor is administered locally or systemically; the TAG72-expressing cells are ovarian cancer cells; and the chimeric antigen receptor is administered by single or repeat dosing.

In various embodiments: the chimeric antigen receptor comprises: a TAG72 scFv (e.g., an scFv comprising the amino acid sequence:

```
                                        (SEQ ID NO: 1)
QVQLVQSGAEVVKPGASVKISCKASGYTFTDHAIHWVKQNPGQRLEWIG

YFSPGNDDFKYNERFKGKATLTADTSASTAYVELSSLRSEDTAVYFCTR

SLNMAYWGQGTLVTVSSGSTSGGGSGGGSGGGGSSDIVMSQSPDSLAVS

LGERVTLNCKSSQSLLYSGNQKNYLAWYQQKPGQSPKLLIYWASARESG

VPDRFSGSGSGTDFTLTISSVQAEDVAVYYCQQYYSYPLTFGAGTKLEL

K with up to 5 or up to10 single amino acid substitutions).
```

In various embodiments: the chimeric antigen receptor comprises: a TAG72 V15 scFv (e.g., an scFv comprising the amino acid sequence:

```
                                        (SEQ ID NO: 33)
QVQLVQSGAEVVKPGASVKISCKASGYTFTDHAIHWVKQNPGQRLEWIG

YFSPGNDDFKYSQKFQGKATLTADTSASTAYVELSSLRSEDTAVYFCTR

SLNMAYWGQGTLVTVSSGSTSGGGSGGGSGGGGSSDIVMSQSPDSLAVS

LGERVTLNCKSSQSVLYSSNSKNYLAWYQQKPGQSPKLLIYWASTRESG

VPDRFSGSGSGTDFTLTISSVQAEDVAVYYCQQYYSYPLSFGAGTKLEL

K with up to 5 or up to 10 single amino acid substitutions).
```

In various embodiments: the chimeric antigen receptor comprises: a TAG72 V59_V15 scFv (e.g., an scFv comprising the amino acid sequence:

```
                                        (SEQ ID NO: 34)
QVQLVQSGAEVKKPGASVKVSCKASGYTFTDHAIHWVRQAPGQRLEWMG

YFSPGNDDFKYSQKFQGRVTITADTSASTAYMELSSLRSEDTAVYFCTR

SLNMAYWGQGTLVTVSSGSTSGGGSGGGSGGGGSSDIVMTQSPDSLAVS

LGERATINCKSSQSLLYSSNSKNYLAWYQQKPGQPPKLLIYWASTRESG

VPDRFSGSGSGTDFTLTISSLQAEDVAVYYCQQPYSYPLSFGAGTKLEL

K with up to 5 or up to 10 single amino acid substitutions).
```

Also described a T cells harboring a vector expressing the CAR. In various embodiments: at least 20%, 30%, or 40% of the transduced human T cells are central memory T cells; at least 30% of the transduced human T cells are CD4+ and CD62L+ or CD8+ and CD62L+; the population of human T cells are autologous to the patient; and the population of human T cells are allogenic to the patient.

TAG72 Targeted CAR

The TAG72 targeted CAR described herein include a TAG72 targeting scFv (e.g., an scFv comprising the amino acid sequence:

(SEQ ID NO: 1)
QVQLVQSGAEVVKPGASVKISCKASGYTFTDHAIHWVKQNPGQRLEWIG
YFSPGNDDFKYNERFKGKATLTADTSASTAYVELSSLRSEDTAVYFCTR
SLNMAYWGQGTLVTVSSGSTSGGGSGGGSGGGGSSDIVMSQSPDSLAVS
LGERVTLNCKSSQSLLYSGNQKNYLAWYQQKPGQSPKLLIYWASARESG
VPDRFSGSGSGTDFTLTISSVQAEDVAVYYCQQYYSYPLTFGAGTKLEL
K or comprising the sequence (SEQ ID NO: 39)
QVQLVQSGAEVVKPGASVKISCKASGYTFTDHAIHWVKQNPGQRLEWIG
YFSPGNDDFKYNERFKGKATLTADTSASTAYVELSSLRSEDTAVYFCTR
SLNMAYWGQGTLVTVSSGSTS and the sequence (SEQ ID NO: 40)
SSDIVMSQSPDSLAVSLGERVTLNCKSSQSLLYSGNQKNYLAWYQQKPG
QSPKLLIYWASARESGVPDRFSGSGSGTDFTLTISSVQAEDVAVYYCQQ
YYSYPLTFGAGTKLELK joined by a flexible linker;

(SEQ ID NO: 33)
QVQLVQSGAEVVKPGASVKISCKASGYTFTDHAIHWVKQNPGQRLEWIG
YFSPGNDDFKYSQKFQGKATLTADTSASTAYVELSSLRSEDTAVYFCTR
SLNMAYWGQGTLVTVSSGSTSGGGSGGGSGGGGSSDIVMSQSPDSLAVS
LGERVTLNCKSSQSVLYSSNSKNYLAWYQQKPGQSPKLLIYWASTRESG
VPDRFSGSGSGTDFTLTISSVQAEDVAVYYCQQYYSYPLSFGAGTKLEL
K; or (SEQ ID NO: 34)
QVQLVQSGAEVKKPGASVKVSCKASGYTFTDHAIHWVRQAPGQRLEWMG
YFSPGNDDFKYSQKFQGRVTITADTSASTAYMELSSLRSEDTAVYFCTR
SLNMAYWGQGTLVTVSSGSTSGGGSGGGSGGGGSSDIVMTQSPDSLAVS
LGERATINCKSSQSLLYSSNSKNYLAWYQQKPGQPPKLLIYWASTRESG
VPDRFSGSGSGTDFTLTISSLQAEDVAVYYCQQPYSYPLSFGAGTKLEL
K.

A useful TAG72 CAR can consist of or comprises the amino acid sequence of SEQ ID NO: 35, 36, or 37 (mature CAR lacking a signal sequence) or the TAG72 CAR can consist of or comprise the amino acid sequence of SEQ ID NO:29, 31, or 32 (immature CAR having a GMCSFRa signal sequence). The CAR can be expressed with additional sequences that are useful for monitoring expression, for example, a T2A skip sequence and a truncated EGFRt. Thus, the CAR can comprise or consist of the amino acid sequence of SEQ ID Nos: 29, 31, or 32 or can comprise or consist of an amino acid sequence that is at least 95%, 96%, 97%, 98% or 99% identical to SEQ ID Nos: 29, 31, or 32. The CAR can comprise or consist of the amino acid sequence of any of SEQ ID Nos: 29, 31, or 32 with up to 1, 2, 3, 4 or 5 amino acid changes (preferably conservative amino acid changes).

Spacer Region

The CAR described herein can include a spacer located between the TAG72 targeting domain (i.e., a TAG72 targeted ScFv or variant thereof) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |
| IgG4 hinge (S→P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (S228P) + linker | 22 aa | ESKYGPPCPPCPGGGSSGGGSG (SEQ ID NO: 5) |
| CD28 hinge | 39 aa | IEVMYPPPYLDNEKSNGTIIHVKGKHLCPSPLFPGPSKP (SEQ ID NO: 6) |
| CD8 hinge-48aa | 48 aa | AKPTTTPAPRPPTPAPTIASQPLSLRPEACRPAAGGAVHTRGLDFACD (SEQ ID NO: 7) |
| CD8 hinge-45aa | 45 aa | TTTPAPRPPTPAPTIASQPLSLRPEACRPAAGGAVHTRGLDFACD (SEQ ID NO: 8) |
| IgG4(HL-CH3) (includes S228P in hinge) | 129 aa | ESKYGPPCPPCPGGGSSGGGSGGQPREPQVYTLPPSQEEMTKNQVSLTCL VKGFYPSDIAVEWESNGQPENNYKTTPPVLDSDGSFFLYSRLTVDKSRWQE GNVFSCSVMHEALHNHYTQKSLSLSLGK (SEQ ID NO: 9) |
| IgG4(L235E,N297Q) | 229 aa | ESKYGPPCPSCPAPEFEGGPSVFLFPPKPKDTLMISRTPEVTCVVVDVSQED PEVQFNWYVDGVEVHQAKTKPREEQFQSTYRVVSVLTVLHQDWLNGKEY KCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGN VFSCSVMHEALHNHYTQKSLSLSLGK (SEQ ID NO: 10) |
| IgG4(S228P, L235E, N297Q) | 229 aa | ESKYGPPCPPCPAPEFEGGPSVFLFPPKPKDTLMISRTPEVTCVVVDVSQED PEVQFNWYVDGVEVHQAKTKPREEQFQSTYRVVSVLTVLHQDWLNGKEY KCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGN VFSCSVMHEALHNHYTQKSLSLSLGK (SEQ ID NO: 11) |

TABLE 1-continued

Examples of Spacers

| Name | Length | Sequence |
|---|---|---|
| IgG4(CH3) | 107 aa | GQPREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQKSL SLSLGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one or more amino acid modifications, for example, 1, 2, 3, 4 or 5 substitutions, e.g., substitutions that reduce off-target binding.

The hinge/linker region can also comprise a IgG4 hinge region having the sequence ESKYGPPCPSCP (SEQ ID NO:4) or ESKYGPPCPPCP (SEQ ID NO:3). The hinge/linger region can also comprise the sequence ESKYGPPCPPCP (SEQ ID NO:3) followed by the linker sequence GGGGSSGGGSG (SEQ ID NO:2) followed by IgG4 CH3 sequence GQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 12). Thus, the entire linker/spacer region can comprise the sequence: ESKYGPPCPPCPGGGSSGGGSGGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHY TQKSLSLSLGK (SEQ ID NO:11). In some cases, the spacer has 1, 2, 3, 4, or 5 single amino acid changes (e.g., conservative changes) compared to SEQ ID NO:11. In some cases, the IgG4 Fc hinge/linker region that is mutated at two positions (L235E; N297Q) in a manner that reduces binding by Fc receptors (FcRs).

Transmembrane Domain

A variety of transmembrane domains can be used in the. Table 2 includes examples of suitable transmembrane domains. Where a spacer region is present, the transmembrane domain is located carboxy terminal to the spacer region.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 13) |
| CD28 | NM_006139 | 27 aa | FWVLVVVGGVLACYSLLVTVAFIIFWV (SEQ ID NO: 14) |
| CD28(M) | NM_006139 | 28 aa | MFWVLVVVGGVLACYSLLVTVAFIIFWV (SEQ ID NO: 15) |
| CD4 | M35160 | 22 aa | MALIVLGGVAGLLLFIGLGIFF (SEQ ID NO: 16) |
| CD8tm | NM_001768 | 21 aa | IYIWAPLAGTCGVLLLSLVIT (SEQ ID NO: 17) |

TABLE 2-continued

Examples of Transmembrane Domains

| Name | Accession | Length | Sequence |
|---|---|---|---|
| CD8tm2 | NM_001768 | 23 aa | IYIWAPLAGTCGVLLLSLVITLY (SEQ ID NO: 18) |
| CD8tm3 | NM_001768 | 24 aa | IYIWAPLAGTCGVLLLSLVITLYC (SEQ ID NO: 19) |
| 41BB | NM_001561 | 27 aa | IISFFLALTSTALLFLLFFLTLRFSVV (SEQ ID NO: 20) |

Costimulatory Domain

The costimulatory domain can be any domain that is suitable for use with a CD3 ζ signaling domain. In some cases the co-signaling domain is a 4-1BB co-signaling domain that includes a sequence that is at least 90%, at least 95%, at least 98% identical to or identical to: KRGRKKLLYIFKQPFMRPVQTTQEEDGCSCRFPEEEEGGCEL (SEQ ID NO:24). In some cases, the 4-1BB co-signaling domain has 1, 2, 3, 4 of 5 amino acid changes (preferably conservative) compared to SEQ ID NO:24.

The costimulatory domain(s) are located between the transmembrane domain and the CD3 ζ signaling domain. Table 3 includes examples of suitable costimulatory domains together with the sequence of the CD3ζ signaling domain.

TABLE 3

CD32 Domain and Examples of Costimulatory Domains

| Name | Accession | Length | Sequence |
|---|---|---|---|
| CD37 | J04132.1 | 113 aa | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 21) |
| CD28 | NM_006139 | 42 aa | RSKRSRLLHSDYMNMTPRRPGPTRKHYQPYAPPRDFAAYRS (SEQ ID NO: 22) |
| CD28gg* | NM_006139 | 42 aa | RSKRSRGGHSDYMNMTPRRPGPTRKHYQPYAPPRDFAAYRS (SEQ ID NO: 23) |
| 41BB | NM_001561 | 42 aa | KRGRKKLLYIFKQPFMRPVQTTQEEDGCSCRFPEEEEGGCEL (SEQ ID NO: 24) |
| OX40 | | 42 aa | ALYLLRRDQRLPPDAHKPPGGGSFRTPIQEEQADAHSTLAKI (SEQ ID NO:25) |

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3 signaling domain and a short linker consisting of 2-10, e.g., 3 amino acids (e.g., GGG) is can be positioned between the costimulatory domain and the CD3 ζ signaling domain.

CD3ζ Signaling Domain

The CD3ζ Signaling domain can be any domain that is suitable for use with a CD3 ζ signaling domain. In some cases, the CD3 ζ signaling domain includes a sequence that is at least 90%, at least 95%, at least 98% identical to or identical to:

(SEQ ID NO: 21)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR.

In some cases, the CD3ζ signaling has 1, 2, 3, 4 of 5 amino acid changes (preferably conservative) compared to SEQ ID NO:21.

Truncated EGFR

The CD3ζ signaling domain can be followed by a ribosomal skip sequence (e.g., LEGGGEGRGSLLTCGD-VEENPGPR; SEQ ID NO:27) and a truncated EGFR having a sequence that is at least 90%, at least 95%, at least 98% identical to or identical to:

(SEQ ID NO: 28)
LVTSLLLCELPHPAFLLIPRKVCNGIGIGEFKDSLSINATNIKHFKNCT

SISGDLHILPVAFRGDSFTHTPPLDPQELDILKTVKEITGFLLIQAWPE

NRTDLHAFENLEIIRGRTKQHGQFSLAVVSLNITSLGLRSLKEISDGDV

IISGNKNLCYANTINWKKLFGTSGQKTKIISNRGENSCKATGQVCHALC

SPEGCWGPEPRDCVSCRNVSRGRECVDKCNLLEGEPREFVENSECIQCH

PECLPQAMNITCTGRGPDNCIQCAHYIDGPHCVKTCPAGVMGENNTLVW

KYADAGHVCHLCHPNCTYGCTGPGLEGCPTNGPKIPSIATGMVGALLLL

LVVALGIGLFM.

In some cases, the truncated EGFR has 1, 2, 3, 4 of 5 amino acid changes (preferably conservative) compared to SEQ ID NO:28.

An amino acid modification refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In some cases, the TAG72 CAR can be produced using a vector in which the CAR open reading frame is followed by a T2A ribosome skip sequence and a truncated EGFR (EGFRt), which lacks the cytoplasmic signaling tail. In this arrangement, co-expression of EGFRt provides an inert, non-immunogenic surface marker that allows for accurate measurement of gene modified cells, and enables positive selection of gene-modified cells, as well as efficient cell tracking of the therapeutic T cells in vivo following adoptive transfer. Efficiently controlling proliferation to avoid cytokine storm and off-target toxicity is an important hurdle for the success of T cell immunotherapy. The EGFRt incorporated in the TAG72 CAR lentiviral vector can act as suicide gene to ablate the CAR+ T cells in cases of treatment-related toxicity.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a lentiviral vector that directs the expression of an TAG72 CAR as well as a non-immunogenic surface marker for in vivo detection, ablation, and potential ex vivo selection. The activated/genetically modified TAG72 central memory T cells can be expanded in vitro with IL-2/IL-15 and then cryopreserved.

DESCRIPTION OF DRAWINGS

FIG. 1A-1D shows cartoon representation of TAG72-BBζ CAR T cells and shows results of TAG72-BBζ CAR T cells cultured with purified TAG72. (A) Diagram of the lentiviral expression cassette with TAG72-CARs containing the humanized scFv (CC49 clone) targeting TAG72, with a 129 amino acid modified human IgG4 Fc linker (void of the CH2 domain, ΔCH2), a CD4 transmembrane domain, a cytoplasmic 4-1BB costimulatory domain, and a cytolytic CD3ζ domain. A truncated non-signaling CD19 (CD19t), separated from the CAR sequence by a T2A ribosomal skip sequence, was expressed for identifying lentivirally transduced T cells. (B) Mock (untransduced) and TAG72-BBζ CAR T cells were evaluated by flow cytometry for CD19t expression to detect lentiviral transduction of CARs (left) or Protein L to detect the scFv (right). (C) CD4 and CD8 expression in Mock (top) and TAG72-BBζ CAR T cells (bottom). (D) Activation (expression of CD137) was assessed by flow cytometry with in vitro stimulated CAR T cells against soluble or plate-bound purified TAG72 antigen for 24 h at indicated protein amounts (units).

FIG. 2A-2B shows results of TAG72-BBζ CAR T cell activation against purified TAG72 antigen. (A) Activation (expression of CD69) was assessed by flow cytometry with in vitro stimulated CAR T cells against soluble or plate-bound purified TAG72 antigen for 24 h at indicated protein amounts (units). (B) IFNγ production by ELISA from TAG72-BBζ CAR T cells against plate-bound purified TAG72 antigen.

FIG. 3A-3H shows results from experiments with TAG72-BBζ CAR T cells cultured with TAG72-positive and TAG72-negative cancer cells. (a) Flow cytometric analysis of TAG72 surface expression on multiple ovarian and colorectal (LS174T) cancer cell lines. (b) Quantification of tumor killing by TAG72-BBζ CAR T cells relative to Mock following a 24 and 72 h co-culture with antigen-positive and -negative tumor targets as described in Materials and Methods. (c) TAG72-BBζ CAR T cell expansion at 24 and 72 h following co-culture with indicated tumor targets. (d,e) IFNγ and IL-2 levels in supernatant quantified by ELISA from Mock or TAG72-BBζ CAR T cells following a 24 and 72 h co-culture with indicated tumor targets. (F) Flow cytometric analysis of TAG72 surface expression on primary human ovarian cancer cells harvested from patient ascites (OAS) after 72 h in culture. (G) Quantification of tumor killing and (H) IFNγ production by TAG72-BBζ CAR T cells relative to Mock following a 72 h co-culture with freshly thawed OAS cells.

FIG. 4 shows results of flow cytometric analysis of TAG72 expression on ascites from OVCAR3 or OV90 tumor-bearing mice.

FIG. 5 shows results TAG72-BBζ CAR T cell-mediated tumor killing of OVCAR3 cells in the presence or absence of 10 units of soluble TAG72 in a 24 h co-culture assay.

FIG. 6A-6F shows results from experiments with regional intraperitoneal delivery of TAG72-BBζ CAR T cells in of OVCAR3 tumor-bearing mice. (A) Schematic illustrating i.p. engraftment of 5.0×106 OVCAR3 (eGFP/ffluc) tumor cells in NSG mice, followed by either i.v. or i.p. delivery of 5.0×106 Mock or TAG72-BBζ CAR T cells on day 14 post tumor injection. (B) Representative bioluminescent flux imaging of mice treated i.v. or i.p. with Mock or TAG72-BBζ CAR T cells. (C) Quantification of flux (each mouse) from OVCAR3 (eGFP/ffluc) tumor-bearing mice treated i.v. or i.p. with Mock or TAG72-BBζ CAR T cells. N=3 per group. (D) Kaplan-Meier survival for Mock and TAG72-BBζ CAR T cell treated mice. N≥4 mice per group. Data are representative of or combined from two independent experiments. (E) Quantification of TAG72-BBζ CAR T cells per uL blood at 6, 13, and 29 days post treatment. N=4 per group. (F) Representative flow cytometric analysis of the frequency of human CD45+ (hCD45) and mouse CD45+ (mCD45) cells in the i.p. cavity of tumor-bearing mice at day 6 and 13 post treatment. Representative images from two independent experiments.

FIG. 7 shows quantification of human CD45+ cells in OVCAR3 model; quantification of human CD45+ cells per uL blood at 6, 13, and 29 days post treatment. N=4 per group.

FIG. 8A-8B shows results of TAG72-BBζ CAR T cells anti-tumor activity in OV90 tumor-bearing mice in vivo delivered either by i.p. or by i.v.; (A) Quantification of flux (each mouse) from OV90 (eGFP/ffluc) tumor-bearing mice treated i.v. or i.p. with Mock or TAG72-BBζ CAR T cells. (B) Kaplan-Meier survival for Mock and TAG72-BBζ CAR T cell treated mice. N≥4 mice per group.

FIG. 9A-9F show results of experiments with either single or repeat regional administration of TAG72-BBζ CAR T cells in OV90 tumor-bearing mice. (A) Schematic illustrating i.p. engraftment of 5.0×106 OV90 (eGFP/ffluc) tumor cells in NSG mice, followed by either single or repeat i.p. treatment with 5.0×106 Mock or TAG72-BBζ CAR T cells on day 8 post tumor infection. (B) Representative bioluminescent flux imaging of mice treated i.p. with a single or repeat treatment of Mock or TAG72-BBζ CAR T cells. (C) Quantification of flux (each mouse) from OV90(eGFP/ffluc) tumor-bearing mice with single or repeat i.p. treatment of Mock or TAG72-BBζ CAR T cells. (D) Analysis of relative tumor growth kinetics at start of treatment (top) and at peak therapy (bottom) time points for all mice. Mann-Whitney test was performed to calculate p values. (E) Kaplan-Meier survival for Mock and TAG72-BBζ CAR T cell treated mice. N≥5 mice per group. (F) Histology of human CD3 cells in tumors harvested from single and repeat treated mice at days 42 and 70 post tumor injection (top: 10× magnification, bottom: 40× magnification). Data are representative of two independent experiments.

FIG. 12 shows the annotated polypeptide sequence of hTag72scFv-IgG4(HL-CH3)-CD4tm-41BB-Zeta-T2A-CD19t (SEQ ID NO:26 with the T2A and CD19t; SEQ ID NO:29 without the T2A and CD19t). SEQ ID NO:35 without the GMCSFRa signal peptide, T2A and CD19t.

FIGS. 14A-14B show results of experiments with either single or repeat regional administration of humanized TAG72 CAR T cells in OV90 tumor-bearing mice. (A) Endogenous expression of TAG72 antigen on OV90 tumor cell line was determined by flow cytometry. OV90-ffluc cells were injected into the intraperitoneal (i.p.) cavity of NSG mice and tracked by bioluminescent imaging and reported as flux (photos/sec). At 8 days post tumor injection, either a single or repeat dose of $5.0\times10^6$ Mock, IDEC, or V15 variants of TAG72 CAR T cells administered regionally into the i.p. cavity of tumor-bearing mice. (B) Tumor burden of single or repeat T cell-treated mice was quantified by bioluminescent imaging. Dashed vertical lines indicate time points of initial and repeated treatment with T cells.

FIGS. 15A-15C show results of i.v. administered humanized TAG72 CAR T cells in OVCAR3 tumor-bearing mice. (A) Endogenous surface TAG72 expression was analyzed by flow cytometry on OVCAR3 tumor cells. OVCAR3-ffluc tumors were then injected into the i.p. cavity of NSG mice, and treated i.v. with a single dose of $5.0\times10^6$ Mock, IDEC, or V15 variant TAG72 CAR T cells. (B) Tumor burden of single dose treated mice was quantified by bioluminescent imaging and reported as flux (photos/sec). Dashed vertical lines indicate time point of treatment with T cells. (C) Quantification of either Mock, or IDEC and V15 TAG72 CAR T cell persistence and proliferation was quantified in the blood by flow cytometry (CAR+ cells per uL of blood) in mice at day 6, 13, and 29 post T cell treatment, and highlight increased persistence and proliferation of V15 variant TAG72 CAR T cells over IDEC.

FIGS. 16A-16E show varying humanized V15-CAR design impacts in vitro antitumor T cell functional activity. (A) CAR expression stability of seven TAG72-CAR T cells variants (with the V15 scFv clone). (B-E) In vitro tumor killing activity, T cell proliferation, CD137+ activation indicator, and PD-1+ exhaustion indicator (72 hours), of CAR T cells against TAG72-negative (DU145, OVCAR8), and TAG72-positive (OVCAR3, OV90, and OVCAR8-sTn) expressing tumor cells.

FIG. 19 shows the annotated polypeptide sequence of Tag72scFv (IDEC)-IgG4 (HL-CH3)-CD4tm-41BB-Zeta without the with the T2A and CD19t (SEQ ID NO:30). SEQ ID NO:35 without the GMCSFRa signal peptide.

FIG. 20 shows the annotated polypeptide sequence of Tag72scFv(v15)-IgG4(HL-CH3)-CD4tm-41BB-Zeta without the with the T2A and CD19t (SEQ ID NO:31). SEQ ID NO:36 without the GMCSFRa signal peptide.

FIG. 21 shows the annotated polypeptide sequence of Tag72scFv (v59_v15)-IgG4 (HL-CH3)-CD4tm-41BB-Zeta without the with the T2A and CD19t (SEQ ID NO:32). SEQ ID NO:37 without the GMCSFRa signal peptide.

DETAILED DESCRIPTION

Figure 11A:
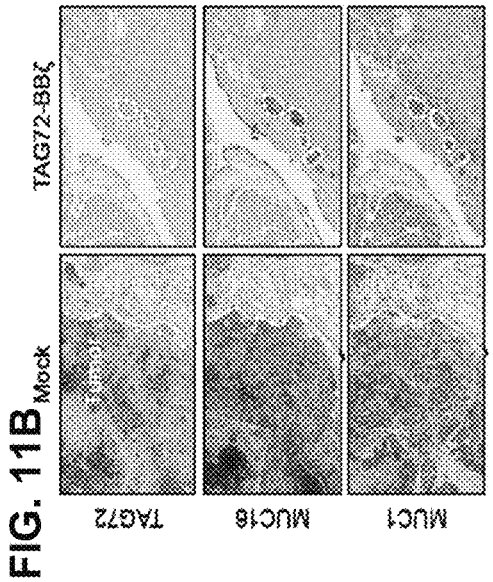
FIG. 11A-11E show results of tumor-associated glycoprotein antigen heterogeneity in ovarian cancer and experiments quantifying CAR T cell-mediated antigen escape. (A) Flow cytometric analysis of TAG72, MUC16, and MUC1 surface expression on OVCAR8, OVCAR3, and OV90 human ovarian cancer cell lines. (B) Histology of TAG72, MUC16, and MUC1 expression in i.p. solid tumors harvested from Mock and TAG72-BBζ CAR T cell treated OVCAR3 tumor-bearing mice at day 99 post treatment. 10× magnification. (C) Histology of TAG72 expression on solid tumors harvested from single and repeat treated OV90 tumor-bearing mice at day 42, 70, and 105 post tumor injection. 10× magnification. (D) Flow cytometric analysis of TAG72 expression in OV90 tumor cells harvested from ascites at indicated time points from mice that received single or repeat i.p. treatment. (E) TAG72 expression on OVCAR3 cells at day 4 following co-culture with Mock or TAG72-BBζ CAR T cells (1:10 E:T ratio), and on tumor cells that grew out at day 28.

In this disclosure the generation and anti-tumor efficacy of a second-generation CAR T cell with a humanized anti-human TAG72 scFv antigen-binding domain and a 4-1BB intracellular co-stimulatory signaling domain (TAG72-BBζ) are described. The TAG72-BBζ CAR T cells exhibited potent antigen-dependent cytotoxicity against multiple TAG72-expressing human ovarian cancer cell lines and epithelial cells derived from patient ovarian cancer ascites grown in cell culture. Regional intraperitoneal in vivo delivery of TAG72-BBζ CAR T cells in peritoneal ovarian tumor models conferred elimination of antigen-positive disease and extension of mice overall survival. In contrast, intravenous CAR T cell delivery was ineffective in controlling disease. Additionally, repeat regional infusions of TAG72-BBζ CAR T cells promoted more durable control of disease compared to single treatment. These preclinical findings support TAG72-BBζ CAR T cells as a viable therapeutic option for ovarian cancers, and also highlight its broader application for multiple TAG72-expressing solid cancers.

EXAMPLES

The invention is further described in the following examples, which do not limit the scope of the invention described in the claims.

Materials and Methods

The following materials and methods were used in the Examples set forth herein.

Cell Lines

The epithelial ovarian cancer line OVCAR3 (ATCC HTB-161) was cultured in RPMI-1640 (Lonza) containing 20% fetal bovine serum (FBS, Hyclone) and 1× antibiotic-antimycotic (1× AA, Gibco) (complete RPMI). The epithelial ovarian cancer line derived from metastatic ascites OV90 (CRL-11732) was cultured in a 1:1 mixture of MCDB 105 medium (Sigma) and Medium 199 (Thermo) adjusted to pH of 7.0 with sodium hydroxide (Sigma) and final 20% FBS and 1×AA. The epithelial-endometroid ovarian cancer line COV362.4 (Sigma) was cultured in Dulbecco's Modified Eagles Medium (DMEM, Life Technologies) containing 10% FBS, 1× AA, 25 mM HEPES (Irvine Scientific), and 2 mM L-Glutamine (Fisher Scientific) (complete DMEM). The epithelial ovarian cancer line OVCAR8 was a generous gift from Dr. Carlotta Glackin at City of Hope and was cultured in complete RPMI-1640. The epithelial ovarian cancer line SKOV3 (ATCC HTB-77) and the colon epithelial cancer line LS174T (ATCC CL-188) were cultured in complete DMEM. All cells were cultured at 37° C. with 5% CO2.

DNA Constructs and Lentivirus Production

Tumor cells were engineered to express enhanced green fluorescent protein and firefly luciferase (eGFP/ffluc) by transduction with epHIV7 lentivirus carrying the eGFP/ffluc fusion under the control of the EF1α promoter as described previously (22). The humanized scFv sequence used in the CAR construct was obtained from a monoclonal antibody clone huCC49 that targets TAG72 (17). The extracellular spacer domain included the 129-amino acid middle-length CH2-deleted version (ΔCH2) of the IgG4 Fc spacer (23). The intracellular co-stimulatory signaling domain contained was a 4-1BB with a CD4 transmembrane domain. The CD3 ζ cytolytic domain was previously described (22). The CAR sequence was separated from a truncated CD19 gene (CD19t) by a T2A ribosomal skip sequence, and cloned in an epHIV7 lentiviral backbone under the control of the EF1α promoter.

Lentivirus was generated as previously described (22, 24). Briefly, 293T cells were transfected with packaging plasmid and CAR lentiviral backbone plasmid using a modified calcium phosphate method. Viral supernatants were collected after 3 to 4 days and treated with 2 mM magnesium and 25 U/mL Benzonase® endonuclease (EMD Millipore). Supernatants were concentrated via high-speed centrifugation and lentiviral pellets were resuspended in phosphate-buffered saline (PBS)-lactose solution (4 g lactose per 100 mL PBS), aliquoted and stored at −80° C. Lentiviral titers were quantified using HT1080 cells based on CD19t expression.

T Cell Isolation, Lentiviral Transduction, and Ex Vivo Expansion

Leukapheresis products were obtained from consented research participants (healthy donors) under protocols approved by the City of Hope Internal Review Board (IRB). On the day of leukapheresis, peripheral blood mononuclear cells (PBMC) were isolated by density gradient centrifugation over Ficoll-Paque (G E Healthcare) followed by multiple washes in PBS/EDTA (Miltenyi Biotec). Cells were rested overnight at room temperature (R T) on a rotator, and subsequently washed and resuspended in X-VIVO T cell medium (Lonza) containing 10% FBS (complete X-VIVO). Up to 5.0×109 PBMC were incubated with anti-CD14 and anti-CD25 microbeads (Miltenyi Biotec) for 30 min at R T and magnetically depleted using the CliniMACS® system (Miltenyi Biotec) according to the manufacturer's protocol and these were termed depleted PBMCs (dPBMC). dPBMC were frozen in CryoStor® CS5 (StemCell Technologies) until further processing.

T cell activation and transduction was performed as described previously (22). Briefly, freshly thawed dPBMC were washed once and cultured in complete X-VIVO containing 100 U/mL recombinant human IL-2 (rhIL-2, Novartis Oncology) and 0.5 ng/ml recombinant human IL-15 (rhIL-15, CellGenix). For CAR lentiviral transduction, T cells were cultured with CD3/CD28 Dynabeads® (Life Technologies), protamine sulfate (APP Pharmaceuticals), cytokine mixture (as stated above) and desired lentivirus at a multiplicity or infection (MOI) of 1 the day following bead stimulation. Cells were then cultured in and replenished with fresh complete X-VIVO containing cytokines every 2-3 days. After 7 days, beads were magnetically removed, and cells were further expanded in complete X-VIVO containing cytokines to achieve desired cell yield. CAR T cells were positively selected for CD19t using the EasySep™ CD19 Positive Enrichment Kit I or II (StemCell Technologies) according to the manufacturer's protocol. Following further expansion, cells were frozen in CryoStor® CS5 prior to in vitro functional assays and in vivo tumor models. Purity and phenotype of CAR T cells were verified by flow cytometry.

Flow Cytometry

For flow cytometric analysis, cells were resuspended in FACS buffer (Hank's balanced salt solution without Ca2+, Mg2+, or phenol red (HBSS−/−, Life Technologies) containing 2% FBS and 1× AA). Cells were incubated with primary antibodies for 30 minutes at 4° C. in the dark. For secondary staining, cells were washed twice prior to 30 min incubation at 4° C. in the dark with either Brilliant Violet 510 (BV510), fluorescein isothiocyanate (FITC), phycoerythrin (PE), peridinin chlorophyll protein complex (PerCP), PerCP-Cy5.5, PE-Cy7, allophycocyanin (APC), or APC-Cy7 (or APC-eFluor780)-conjugated antibodies. Antibodies against CD3 (BD Biosciences, Clone: SK7), CD4 (BD Biosciences, Clone: SK3), CD8 (BD Biosciences, Clone: SK1), CD14 (BD Biosciences, Clone: MP9), CD19 (BD Biosciences, Clone: SJ25C1), CD25 (BD Biosciences, Clone: 2A3), mouse CD45 (BioLegend, Clone: 30-F11), CD45 (BD Biosciences, Clone: 2D1), CD69 (BD Biosciences, Clone: L78), CD137 (BD Biosciences, Clone: 4B4-1), MUC1 (BioLegend, Clone 16A), MUC16 (Abcam, Clone X75 or EPSISR23), biotinylated Protein-L (GenScript USA) (25), TAG72 (Clone, muCC49), Donkey Anti-Rabbit Ig (Invitrogen), Goat Anti-Mouse Ig (BD Biosciences), and streptavidin (BD Biosciences) were used. Cell viability was determined using 4', 6-diamidino-2-phenylindole (DAPI, Sigma). Flow cytometry was performed on a MACSQuant Analyzer 10 (Miltenyi Biotec), and the data was analyzed with FlowJo software (v10, TreeStar).

In Vitro Tumor Killing and T Cell Functional Assays

For tumor killing assays, CAR T cells and tumor targets were co-cultured at indicated effector:tumor (E:T) ratios in complete X-VIVO in the absence of exogenous cytokines in 96-well plates for 24 to 72 h and analyzed by flow cytometry as described above. Tumor killing by CAR T cells was calculated by comparing CD45-negative cell counts relative to that observed when targets were co-cultured with Mock (untransduced) T cells. For T cell activation assays, CAR T cells and tumor targets were co-cultured at the indicated E:T ratios in complete X-VIVO in the absence of exogenous cytokines in 96-well plates for the indicated time points and analyzed by flow cytometry for specific markers of T cell activation. Frozen, uncultured patient primary ovarian cancer ascites (OAS3, OAS4, and OAS7) were thawed, directly analyzed for TAG72 expression, and evaluated in T cell functional assays. Briefly, ascites fluid from ovarian cancer patients was obtained from City of Hope National Medical Center (COH) surgical staff in a sterile vacuum container with approval from the COH Institutional Review Board (IRB) and Office of Human Subjects Protection. The COH IRB waived the need for written informed consent as all samples were de-identified and ascites was discard material as previously described (26).

For T cell activation assays on plate-bound antigen, purified soluble TAG72 antigen (BioRad) was plated in duplicate at indicated TAG72 units overnight at 4° C. in 1×PBS in 96-well flat bottom high-affinity plates (Corning). A total of 104 TAG72-BBζ CAR T cells were then added in a fixed volume of 100 µL to each well and incubated for indicated times prior to collection of cells for analysis of activation markers (CD69, CD137) by flow cytometry. Supernatants were also collected for analysis of cytokine production.

ELISA Cytokine Assays

Supernatants from tumor killing assays or CAR T cell activation assays on plate-bound TAG72 antigen were collected at indicated times and frozen at −20° C. for further use. Supernatants were then analyzed for secreted human IFNγ and IL-2 according to the Human IFNγ and IL-2 ELISA Ready-SET-GO!® ELISA kit manufacturer's protocol, respectively. Plates were read at 450 nm using a Wallac Victor3 1420 Counter (Perkin-Elmer) and the Wallac 1420 Workstation software.

In Vivo Tumor Studies

All animal experiments were performed under protocols approved by the City of Hope Institutional Animal Care and Use Committee. For in vivo tumor studies, OVCAR3 and OV90 cells (5.0×106) were prepared in a final volume of 500 µl HBSS−/− and engrafted in 6 to 8 week old female NSG mice by intraperitoneal (i.p.) injection. Tumor growth was monitored at least once a week via biophotonic imaging (Xenogen, LagoX) and flux signals were analyzed with Living Image software (Xenogen). For imaging, mice were i.p. injected with 150 µL D-luciferin potassium salt (Perkin Elmer) suspended in PBS at 4.29 mg/mouse. Once flux signals reached desired levels, day 8 for OV90 and day 14 for OVCAR3, T cells were prepared in 1×PBS, and mice were treated with 500 µL i.p. or 200 µL intravenous (i.v.) injection of 5.0×106 Mock or TAG72-BBζ CAR T cells. In the OV90 tumor model, we tested the impact of repeat treatment with i.p. TAG72-BBζ CAR T cells starting at day 8, followed by treatments at additional indicated days post tumor engraftment. Humane endpoints were used in determining survival. Mice were euthanized upon signs of distress such as a distended belly due to ascites, labored or difficulty breathing, apparent weight loss, impaired mobility, or evidence of being moribund. At pre-determined time points or at moribund status, mice were euthanized and tissues and/or ascites fluid were harvested and processed for flow cytometry and immunohistochemistry as described below.

Peripheral blood was collected from isoflurane-anesthetized mice by retro-orbital (RO) bleed through heparinized capillary tubes (Chase Scientific) into polystyrene tubes containing a heparin/PBS solution (1000 units/mL, Sagent Pharmaceuticals). Volume of each RO blood draw (approximately 120 µL/mouse) was recorded for cell quantification per µL blood. Red blood cells (RBCs) were lysed with 1× Red Cell Lysis Buffer (Sigma) according to the manufacturer's protocol and then washed, stained, and analyzed by flow cytometry as described above. Cells from i.p. ascites fluid was collected from euthanized mice by injecting 5 mL cold 1×PBS into the i.p. cavity, which was drawn up via syringe and stored on ice until further processing. RBC-depleted ascites was washed, stained, and analyzed by flow cytometry for tumor-associated glycoprotein expression and CAR T cells using antibodies and methods described above.

Immunohistochemistry

Tumor tissue was fixed for up to 3 days in 4% paraformaldehyde (4% PFA, Boston BioProducts) and stored in 70% ethanol until further processing. Immunohistochemistry was performed by the Pathology Core at City of Hope. Briefly, paraffin-embedded sections (10 µm) were stained with hematoxylin & eosin (H&E, Sigma-Aldrich), mouse anti-human CD3 (DAKO), mouse anti-human TAG72 (AB16838, Abcam), rabbit anti-human MUC1 (AB45167, Abcam), MUC16 (AB1107, Abcam). Images were obtained using the Nanozoomer 2.0HT digital slide scanner and the associated NDP.view2 software (Hamamatzu).

Statistical Analysis

Data are presented as mean±SEM, unless otherwise stated. Statistical comparisons between groups were performed using the unpaired two-tailed Student's t test to calculate p value, unless otherwise stated. *p<0.05, p<0.01, *p<0.001; NS, not significant.

Example 1: Construction of TAG72-CAR T Cells Containing a 4-1BB Intracellular Co-Stimulatory Domain and Validation that TAG72-BBζ CAR T Cells Exhibit Activity Against TAG72

To determine if TAG72-CAR T cells containing a 4-1BB intracellular co-stimulatory domain effectively demonstrate activation against purified TAG72, the aforementioned cells were grown in presence of increasing amounts of either soluble TAG72 or plate-bound TAG72 and CD137 expression, an indicator of activation, was measured.

Results

TAG72-BBζ CAR lentivirus was used to transduce human healthy donor-derived peripheral blood mononuclear cells depleted of CD14+ and CD25+ cells (dPBMC), as previously described (Priceman S J, Gerdts E A, Tilakawardane D, Kennewick K T, Murad J P, Park A K, Jeang B, Yamaguchi Y, Yang X, Urak R, Weng L, Chang W C, Wright S, Pal S, Reiter R E, Wu A M, Brown C E, Forman S J. Co-stimulatory signaling determines tumor antigen sensitivity and persistence of CAR T cells targeting PSCA+ metastatic prostate cancer. Oncoimmunology. 2018; 7 (2): e1380764). TAG72-BBζ CAR T cells were enriched during the manufacturing process (based on CD19t+ selection) and were stably expressed on the surface of T cells (FIG. 1B). CAR T cells expanded ex vivo with similar kinetics and comparable CD4:CD8 ratios to Mock (untransduced) T cells (FIG. 1C). Importantly, and as a first measure of CAR T cell activation against TAG72, TAG72-BBζ CAR T cells exhibited dose-dependent CD137 expression on the surface when cultured with plate-bound, but not soluble, purified TAG72 (FIG. 1D). Additionally, TAG72-BBζ CAR T cells exhibited dose-dependent induction of other activator indicators, specifically cell-surface CD69 expression and IFNγ release, when cultured with plate-bound TAG72, but not soluble, purified TAG72 (FIG. 2).

Example 2: Validation that TAG72-BBζ CAR T Cells Selectively Target and Exhibit Activation Against TAG72-Positive Ovarian Cancer Cells In Vitro To determine if TAG72-BBζ CAR T cells demonstrate selective activity against TAG72-positive cancer cells, the TAG72-BBζ CAR T cells were grown in presence of either TAG72-positive or TAG72-negative ovarian cancer cells and the percentage of ovarian cancer cells killed was quantified.

Results

As a first step toward evaluating TAG72-BBζ CAR T cells selective activity—including targeting and conferring cell death of target cells—against TAG72-positive cancer cells, TAG72 expression on human ovarian cancer cell lines, including SKOV3, OVCAR8, COV362.4, OVCAR3, OV90, as well as the TAG72+ colon cancer line, LS174T, was evaluated to identify a TAG72-positive cancer cell line. Prior studies have demonstrated expression of TAG72 by immunohistochemistry of ovarian tumor patient samples and by western blotting of human ovarian cancer cell lines (Chauhan S C, Vinayek N, Maher D M, Bell M C, Dunham K A, Koch M D, Lio Y, Jaggi M. Combined staining of TAG-72, MUC1, and CA125 improves labeling sensitivity in ovarian cancer: antigens for multi-targeted antibody-guided therapy. The journal of histochemistry and cytochemistry: official journal of the Histochemistry Society. 2007; 55 (8): 867-75; Ponnusamy M P, Venkatraman G, Singh A P, Chauhan S C, Johansson S L, Jain M, Smith L, Davis J S, Remmenga S W, Batra S K. Expression of TAG-72 in ovarian cancer and its correlation with tumor stage and patient prognosis. Cancer letters. 2007; 251 (2): 247-57). By flow cytometry, TAG72 was expressed on OVCAR3 cells (approximately 42%) and to a greater extent on OV90 cells (approximately 90%), with very low levels detected on COV362.4 cells (FIG. 3A). TAG72 was absent on SKOV3 and OVCAR8 cells. Immunofluorescence staining of tumor cells confirmed TAG72 expression and cellular localization on the cell surface as well as intracellularly. Notably, higher expression of TAG72 on OVCAR3 and OV90 cells harvested from the ascites of tumor-bearing animals was observed as compared to in vitro cultured cells (FIG. 4).

To assess antigen-dependent activity of our TAG72-BBζ CAR T cells, co-cultured assays with TAG72-positive and -negative ovarian tumor targets were conducted at an E:T ratio between 1:1 and 1:2 to determine their killing potential. After 24 hours, antigen-specific T cell-mediated killing activity was evident with TAG72-BBζ CAR T cells relative to Mock T cells (FIG. 3B). Amongst TAG72-expressing targets, an average of 59% LS174T, 79% OVCAR3, and 67% OV90 cells were killed. After 72 hours, killing of the same tumor lines increased to 77%, 90%, and 97%, respectively. TAG72-BBζ CAR T cells showed minimal killing of TAG72-negative or low expressing SKOV3, OVCAR8, and COV362.4 cells. At 72 hours, TAG72-BBζ CAR T cell expansion against TAG72-positive tumor cells was 2- to 3-fold (FIG. 3C). Similar tumor killing was observed at lower E:T ratios of 1:10, demonstrating the potent killing ability of TAG72-BBζ CAR T cells. The tumor killing ability of TAG72-BBζ CAR T cells was minimally impacted by soluble TAG72 shed from tumor cells (FIG. 5). Cytokine production from CAR T cells was measured as an additional measure of T cell activity. IFNγ and IL-2 cytokine production was observed only when TAG72-BBζ CAR T cells were co-cultured with antigen-positive tumor targets, OVCAR3, LS174T, and OV90 (FIGS. 3D and 3E). While IL-2 production peaked at early time points (T=24 hour) and was detectable only against OVCAR3 at later time points (T=72 hours), in contrast IFNγ levels exhibited elevated levels over the full 72 hours.

Example 3: Validation that TAG72-BBζ CAR T Cells Selectively Target TAG72-Positive Cells from Ovarian Cancer Ascites In Vitro To further confirm TAG72 as an ovarian cancer CAR target and the anti-tumor activity of our TAG72-BBζ CAR T cells, TAG72-BBζ CAR T cells were grown in presence of human ovarian cancer ascites from three patients (OAS3, OAS4, OAS7).

Results

Freshly thawed ascites from OAS3, OAS4, and OAS7 expressed 62%, 80%, and 67% TAG72, respectively, by flow cytometry, but after 72 hours in culture, was reduced to 2%, 53%, and 19%, respectively (FIG. 3F). Without wishing to be bound to a particular theory, the reduction in TAG72 expression may reflect an influence of ex vivo culturing conditions on maintenance of TAG72 expression (Horan Hand P, Colcher D, Salomon D, Ridge J, Noguchi P, Schlom J. Influence of spatial configuration of carcinoma cell populations on the expression of a tumor-associated glycoprotein. Cancer research. 1985; 45 (2): 833-40). TAG72-BBζ CAR T cells exhibited cytolytic activity after 72 hours of co-culture with ascites, and showed potent and selective CAR-mediated killing of the TAG72-positive OAS4 and OAS7 cells, with no detectable anti-tumor activity against the TAG72-negative OAS3 cells (FIG. 3G). TAG72-BBζ CAR T cells produced IFNγ and IL-2 against OAS4, but not OAS3 and OAS7 cells (FIG. 3H). These data suggest that TAG72-CAR T cells selectively target TAG72-positive cells from ovarian cancer ascites in vitro.

Example 4: Validation that TAG72-BBζ CAR T Cells Delivered Locally to Ovarian Ascites In Vivo in a Mouse Model Exhibit Potent Anti-Tumor Activity and Confer Extended Lifespan to the Mice To evaluate the therapeutic potential of the TAG72-BBζ CAR T cells in vivo, the ability of TAG72-BBζ CAR T cells to selectively target TAG72-positive OVCAR3 tumors in immune compromised NSG mice was tested; this mouse model mimics mimic peritoneal ovarian tumors observed in late-stage human disease. The TAG72-BBζ CAR T cells were delivered by intraperitoneal (i.p.) injection.

Results

OVCAR3 cells were lentivirally transduced to express eGFP/ffluc to allow for tracking of tumor growth via non-invasive optical imaging. At 14 days post tumor i.p. injection, mice were treated with Mock or TAG72-BBζ CAR T cells ($5.0 \times 10^6$) by systemic intravenous (i.v.) or regional i.p. delivery (FIG. 6A). Rapid anti-tumor effects were observed in mice treated with TAG72-BBC CAR T cells via regional i.p. delivery, reaching a maximal anti-tumor response 1-2 weeks following treatment (FIGS. 6B and 6C). In comparison to regional delivery, i.v. delivery of TAG72-BBζ CAR T cells showed limited anti-tumor responses. Anti-tumor responses in mice were durable for 3-4 weeks, but ultimately tumor recurrences were observed in mice. Regional i.p. delivery of TAG72-BBζ CAR T cells significantly extended survival of mice, with limited benefits observed by i.v. delivery (FIG. 6D).

To address potential differences observed between i.p. and i.v. therapy, CAR T cells in the blood and ascites of mice were quantified. Strikingly, appreciable numbers of CAR T cells (huCD45+CD19t+) were found in the blood of mice 6 days post i.p. treatment, with more than 5-fold fewer CAR T cells in the blood of i.v. treated mice at the same time point (FIG. 6E and FIG. 7). However, equivalent numbers of CAR T cells were observed in the blood of i.p. and i.v. treated mice at later time points, expanding from 1-2 weeks, with significant reductions at 4 weeks post treatment. CAR T cells in the ascites of treated mice continued to be present at the site of tumors at day 6 post i.p. treatment, with no detectable CAR T cells in i.v. treated mice at the same time point. However, at day 13 post treatment, similar levels of CAR T cells were observed in mice treated i.v. and i.p. (FIG. 6F). Without wishing to be bound to a particular theory, these data collectively suggest that CAR T cells eventually reached the tumor following i.v. delivery but with delayed kinetics compared with i.p. delivery, which was likely in part responsible for the lack of observed therapy by this route of administration. CD45-negative cells, likely majority being OVCAR3 tumor cells, were significantly depleted in i.p. TAG72-BBζ CAR T cell treated mice, but not i.p. or i.v. Mock T cell or i.v. TAG72-BBζ CAR T cell treated mice. These data support regional intraperitoneal delivery of TAG72-CAR T cells as an effective method of targeting peritoneal ovarian tumors in mice.

Example 5: Validation that TAG72-BBζ CAR T Cells Selectively Target TAG72-Positive Cells in OV90 i.p. Model and Comparison of Efficacy for TAG72-BBζ CAR T Cells Administered as Single Versus Multiple Dosing Regimen To evaluate efficacy of TAG72-BBζ CAR T cells to selective target TAG72-positive cells in the OV90 i.p. model, TAG72-BBζ CAR T cells were delivered either as single or multiple repeat doses and tumor size was evaluated over time.
Results Notably, the OV90 i.p. model exhibits more uniform TAG72 expression in vitro compared with OVCAR3 (FIG. 3A). Regional CAR T cell delivery in the OV90 i.p. model showed selective targeting of TAG72 cells compared to the OVCAR3 model, i.p . . . . In contrast, i.v. TAG72-BBζ CAR T cell treatment failed to show anti-tumor efficacy in the OV90 model (FIG. 8). Overall survival was only delayed by approximately 25 days in this model with i.p. delivery of TAG72-BBζ CAR T cells (FIG. 8), likely owing to the aggressive nature of this model. Given this observation, the efficacy of repeat TAG72-BBζ CAR T cell dosing compared with a single dose was evaluated and found to improve therapeutics responses (FIG. 9A). Compared with a single dose of TAG72-BBζ CAR T cells, repeat dosing over the course of one month demonstrated more durable anti-tumor responses in the OV90 model (FIGS. 9B and 9C). When plotted as relative tumor growth kinetics, repeat dosing promoted more extensive tumor regression as well as more durable control of tumors compared with single dosing (FIG. 9D).

Figure 10D:
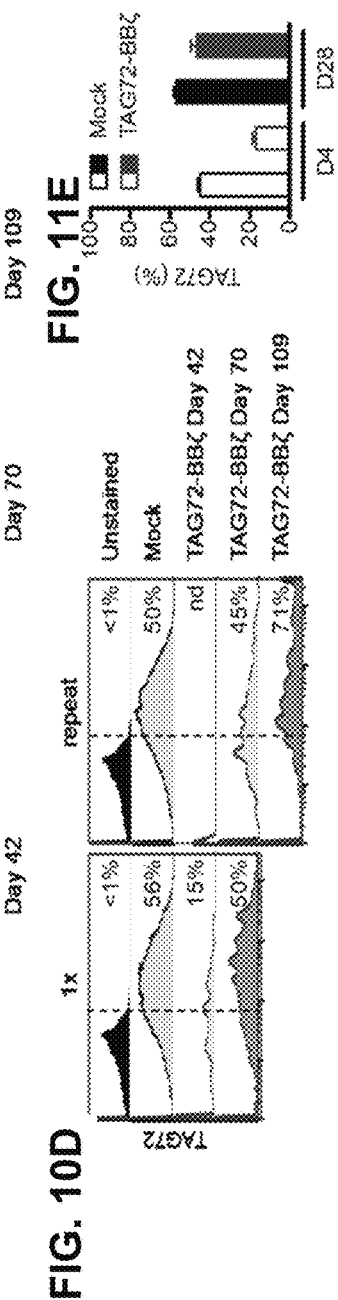
FIG. 10A-10B shows quantification of human CD45+ cells in OV90 model; quantification of human CD45+ cells per uL blood at 7, 14, and 34 days post treatment. N=4 per group.

In this study, the overall survival was extended significantly in mice that received repeat doses of TAG72-BBζ CAR T cells (55 day benefit) compared with a single dose (30 day benefit) (FIG. 9E). Greater T cell numbers were observed in peritoneal tumors of mice with repeat treatment (FIG. 9F). Importantly, however, reduced numbers, expansion and persistence of CAR T cells in the blood of OV90-bearing mice was observed compared with the OVCAR3 model (FIG. 10). Without wishing to be bound to a particular theory, these results suggest that this more aggressive tumor model may also harbor suppressive mechanisms that hamper T cell function and overall CAR T cell efficacy. Collectively, these data demonstrate potent anti-tumor activity of TAG72-BBζ CAR T cells in ovarian cancer xenograft models, and also suggest that repeat dosing of regionally delivered CAR T cells may provide greater control of tumors compared with a single dose.

Figure 11B:
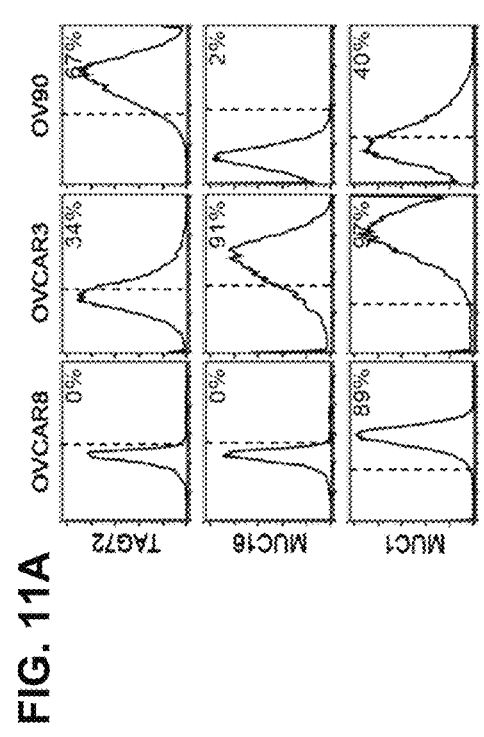
Figure 11:
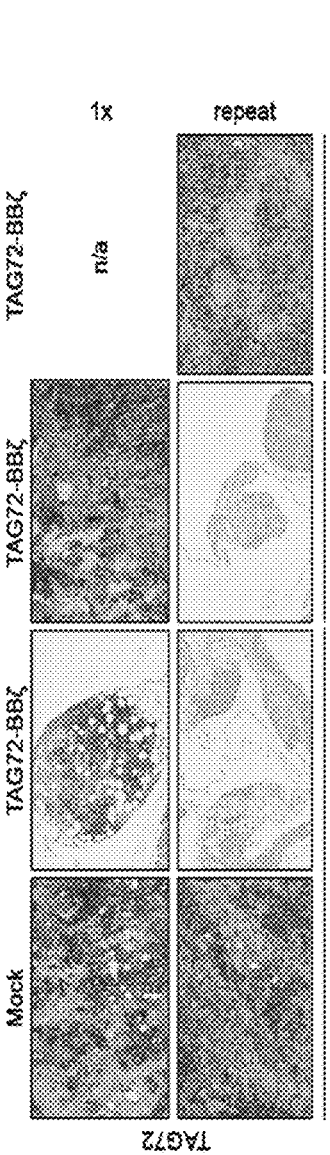
Figure 11E:
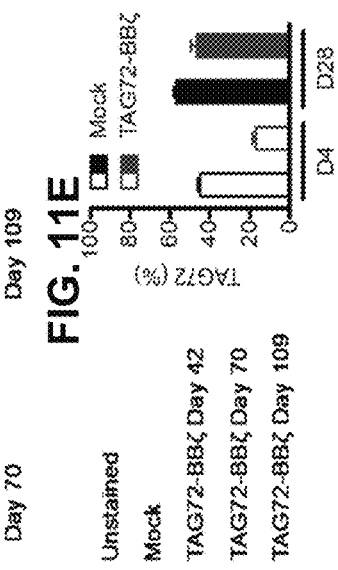

Example 6: Determination that Tumor Recurrences Following TAG72-CAR T Cell Therapy Exhibit Antigen Escape Given that TAG72-BBζ CAR T cells in previous Examples were observed to reduce prior to tumor recurrences, the expression of TAG72 in tumors was quantified over time to determine if loss of TAG72 expression correlates with reduced TAG72-BBζ CAR T cell numbers.
Results One of the major resistance mechanisms to CAR T cell therapy is the tumor antigen heterogeneity that exists in solid tumors that promotes eventual antigen loss or escape (Chen N, Li X, Chintala N K, Tano Z E, Adusumilli P S. Driving CARs on the uneven road of antigen heterogeneity in solid tumors. Current opinion in immunology. 2018; 51:103-10). Given that the loss of CAR T cells in the two in vivo models (of previous Examples) preceded tumor recurrences, potentially loss of TAG72 expression in tumors occurs correlates with loss of CAR T cells. To evaluate the former, the expression of TAG72 in tumors from Mock and TAG72-BBζ CAR T cell treated mice was measured over time pre- and post-therapy. Since TAG72, MUC1, and MUC16 have all been identified as potential targets in ovarian cancer, the expression of these cell surface antigens on TAG72-negative OVCAR8, and TAG72-positive OVCAR3 and OV90 cells was quantified. OVCAR8 appeared to only express low levels of MUC1, and was absent for TAG72 and MUC16, while OVCAR3 expressed all three antigens at varying levels, and OV90 showed low expression of MUC1 and was absent for MUC16 (FIG. 11A). Therefore, the expression of these antigens in OVCAR3 tumors from mice treated with Mock or TAG72-BBζ CAR T cells was quantified. At twelve weeks post T cell infusion, tumors from Mock-treated mice showed heterogeneous expression of TAG72 (similar to flow cytometry analysis of the cell line), MUC16, and MUC1 (FIG. 11B). However, tumor recurrences at early time points from mice treated with TAG72-BBζ CAR T cells showed a dramatic reduction in TAG72 expression, while maintaining expression of MUC16 and MUC1. Similarly, repeat treatment of TAG72-BBζ CAR T cells in the OV90 tumor model also showed a reduction in TAG72 expression in early recurrent tumors following treatment (FIG. 11E). Notably, the expression of TAG72 was detected at high levels in tumor recurrences at later time points, in solid tumors as well as in ascites (FIGS. 11C and 11D). To further confirm this finding in vitro, the expression of TAG72 in tumor cells following CAR T cell co-culture was quantified and found to be reduced compared to tumor cells that grew out in the absence of co-culture with CAR T cells (FIG. 11E). In total, these data suggest that antigen escape likely plays a key role in tumor recurrences following TAG72-BBζ CAR T cell therapy.

Figure 13A:
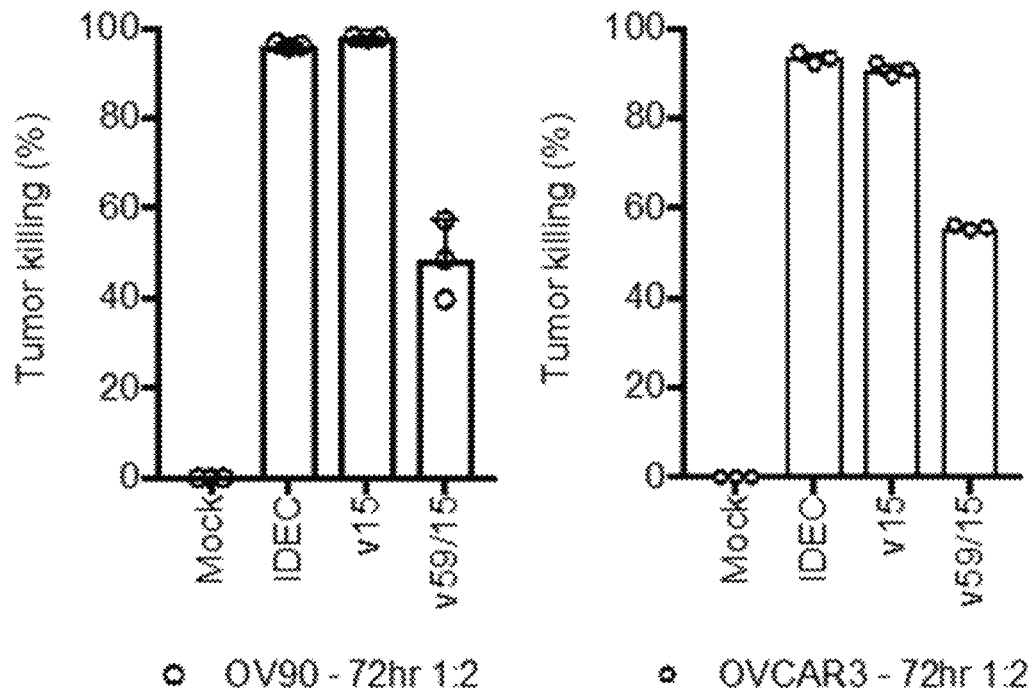
FIGS. 13A-13C show tumor killing, activation, and T cell proliferation of humanized TAG72 CAR T cells. (A) OV90 and OVCAR3 cells were co-cultured for 72 hours with either Mock, IDEC, V15 or V59/15 variant TAG72 CAR T cells at an E:T of 1:2. Tumor killing is represented as % killing relative to mock-treated conditions. (B) T cell activation was analyzed from 72 hour co-culture assays by flow cytometry staining of surface CD137 expression. (C) T cell proliferation (fold expansion) at 72 hours was determined relative to T cell counts plated on day 0.
Figure 13B:
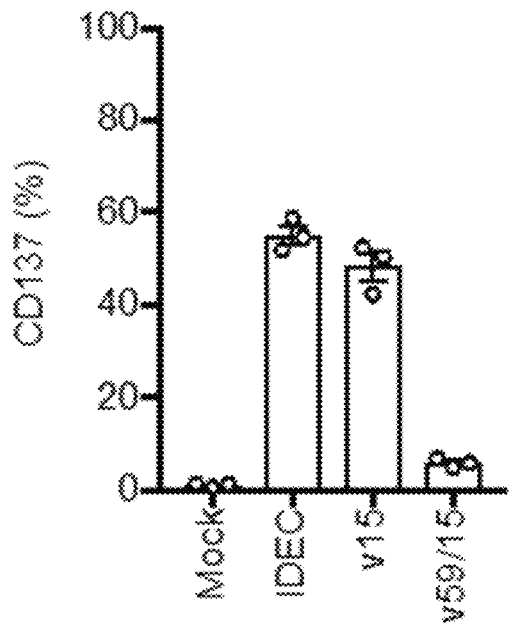
Figure 13C:
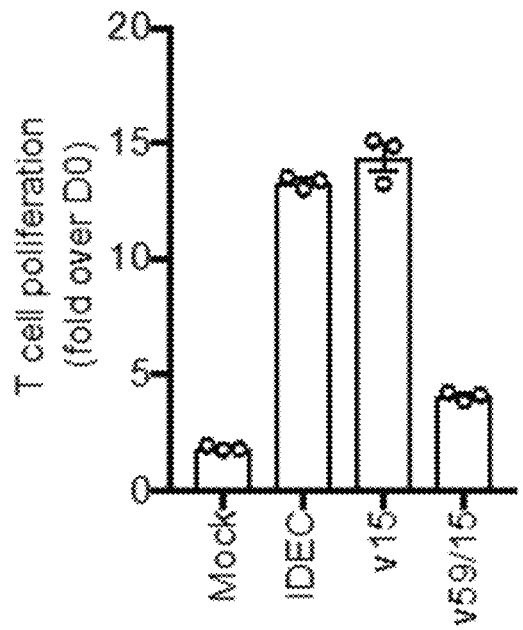

Example 7: Validation that TAG72-BBζ CAR T Cells Selectively Target and Exhibit Activation Against TAG72-Positive Ovarian Cancer Cells In Vitro To determine if humanized TAG72-BBζ CAR T cells also effectively kill TAG72-positive cancer cells, humanized TAG72-BBζ CAR T cells were grown in presence of TAG72-positive ovarian cancer cells and the percentage of ovarian cancer cells killed was quantified.
Results A series of representative 4-1BB co-stimulated CAR T cells that expresses either the IDEC, V15, or a combined V59/V15 antigen-binding domain (scFv) from humanized variants of anti-TAG-72 antibody clone CC49 (IDEC-TAG72-BBz, V15-TAG72-BBz, or V59/15-TAG72-BBz; FIGS. 19-21 (shown without the T2A and CD1t sequences present at the carboxy terminus) were created. These CARs all utilize the same extracellular domain (composed of IgG4 hinge with a mutation to P at amino acid 10 of the hinge; a linker having the sequence GGGSSGGGSG and the human IgG CH3 domain), a CD4 transmembrane domain, and a 4-1BB intracellular co-stimulatory signaling domain. These humanized TAG72-BBζ CAR T cells were grown in presence of either OV90 or OVCAR3 ovarian cancer cells and the percentage of ovarian cancer cells killed was quantified. In vitro, both the IDEC and V15 TAG72-BBz CAR T cells show equivalent potent T cell-mediated antigen-dependent cytotoxicity, activation, and T cell proliferation following exposure to TAG72-expressing ovarian cancer cell lines (FIG. 13A-13C). The V59/15 TAG72-BBz CARs showed little activity in this assay and was removed from further experiments.

Example 8: Validation that Humanized TAG72-BBζ CAR T Cells Selectively Target TAG72-Positive Cells in OV90 i.p. Model and Comparison of Efficacy for TAG72-BBζ CAR T Cells Administered as Single Versus Multiple Dosing Regimen To evaluate efficacy of humanized TAG72-BBζ CAR T cells to selective target TAG72-positive cells in the OV90 i.p. model, humanized TAG72-BBζ CAR T cells were delivered either as single or multiple repeat doses and tumor size was evaluated over time.

Results

Endogenous expression of TAG72 antigen on OV90 tumor cell line was determined by flow cytometry. OV90-ffluc cells were injected into the intraperitoneal (i.p.) cavity of NSG mice and tracked by bioluminescent imaging and reported as flux (photos/sec). At 8 days post tumor injection, either a single or repeat dose of $5.0\times10^6$ Mock, IDEC, or V15 variants of TAG72 CAR T cells administered regionally into the i.p. cavity of tumor-bearing mice (FIG. 14A). Tumor burden of single or repeat T cell-treated mice was quantified by bioluminescent imaging. Dashed vertical lines indicate time points of initial and repeated treatment with T cells. Interestingly, we show using in vivo ovarian tumor models that regional intraperitoneal treatment with V15-TAG72-BBz reduces tumor burden of antigen-positive targets (OV90 engrafted tumors) to a greater extent than IDEC-TAG72-BBz CARs (FIGS. 14A-14B). Given this observation, the efficacy of repeat TAG72-BBζ CAR T cell dosing compared with a single dose was evaluated and found to improve therapeutics responses (FIG. 14B). Compared with a single dose of TAG72-BBζ CAR T cells, repeat dosing over the course of over 50 days demonstrated more durable anti-tumor responses in the OV90 model (FIG. 14B).

Example 9: Validation that Humanized TAG72-BBζ CAR T Cells Selectively Target TAG72-Positive Cells in OVCAR3 i.p. Model and Comparison of Persistence for TAG72-BBζ CAR T Cells Administered as a Single Dosing Regimen To evaluate efficacy of humanized TAG72-BBζ CAR T cells to selective target TAG72-positive cells in the OVCAR3 i.p. model, humanized TAG72-BBζ CAR T cells were delivered as a single dose and tumor size was evaluated over time.

Results

Endogenous surface TAG72 expression was analyzed by flow cytometry on OVCAR3 tumor cells. OVCAR3-ffluc tumors were then injected into the i.p. cavity of NSG mice, that were treated i.v. with a single dose of $5.0\times10^6$ Mock, IDEC, or V15 variant TAG72 CAR T cells (FIG. 15A). Tumor burden of single dose treated mice was quantified by bioluminescent imaging and reported as flux (photos/sec). Dashed vertical lines indicate time point of treatment with T cells. Interestingly, intravenously (i.v.) administered V15-TAG72-BBz CAR T cells, but not IDEC-TAG72-BBz CAR T cells, are able to mediate a robust anti-tumor response against OVCAR3 tumor bearing mice (FIG. 15B). This anti-tumor response in vivo of the V15-TAG72-BBz CARs was in part mediated by an increased proliferation compared to IDEC-TAG72-BBz, thus increasing the longevity of its response (FIG. 15C).

Example 10: Determination that Humanized TAG72-BBζ CAR T Cells Design Affects Tumor Killing, T Cell Proliferation, Activation, Exhaustion, and Cytokine Production To evaluate the design of humanized TAG72 CAR T cells, a series of representative TAG72 CAR T cells was created featuring the V15 scFv and varying the linker, transmembrane, and costimulatory domains.

Results

All seven representative humanized TAG72-CAR T cells variants with the V15 scFv clone exhibited CAR expression stability (FIG. 16A). In an in vitro tumor killing activity, humanized TAG72-CAR T cells were grown in presence of either TAG72-positive (OVCAR3, OV90, and OVCAR8-sTn) or TAG72-negative (DU145, OVCAR8) ovarian cancer cells and the percentage of ovarian cancer cells killed was quantified. All seven representative humanized TAG72-CAR T cells variants showed potent and selective CAR-mediated killing of the TAG72-positive OVCAR3, OV90, and OVCAR8-sTn cells, with no detectable anti-tumor activity against the TAG72-negative DU145 and OVCAR8 cells (FIG. 16B). T cell proliferation varied and was higher in the TAG72-positive OVCAR3, OV90, and OVCAR8-sTn cells than in the TAG72-negative DU145 and OVCAR8 cells (FIG. 16C). CD137+ activation indicator showed that the representative humanized TAG72-CAR T cells variants varied and was higher in the TAG72-positive OVCAR3, OV90, and OVCAR8-sTn cells than in the TAG72-negative DU145 and OVCAR8 cells (FIG. 16D). PD-1+ exhaustion indicator (72 hours) of CAR T cells against TAG72-negative (DU145, OVCAR8), and TAG72-positive (OVCAR3, OV90, and OVCAR8-sTn) expressing tumor cells (FIG. 16E).

Figure 17:
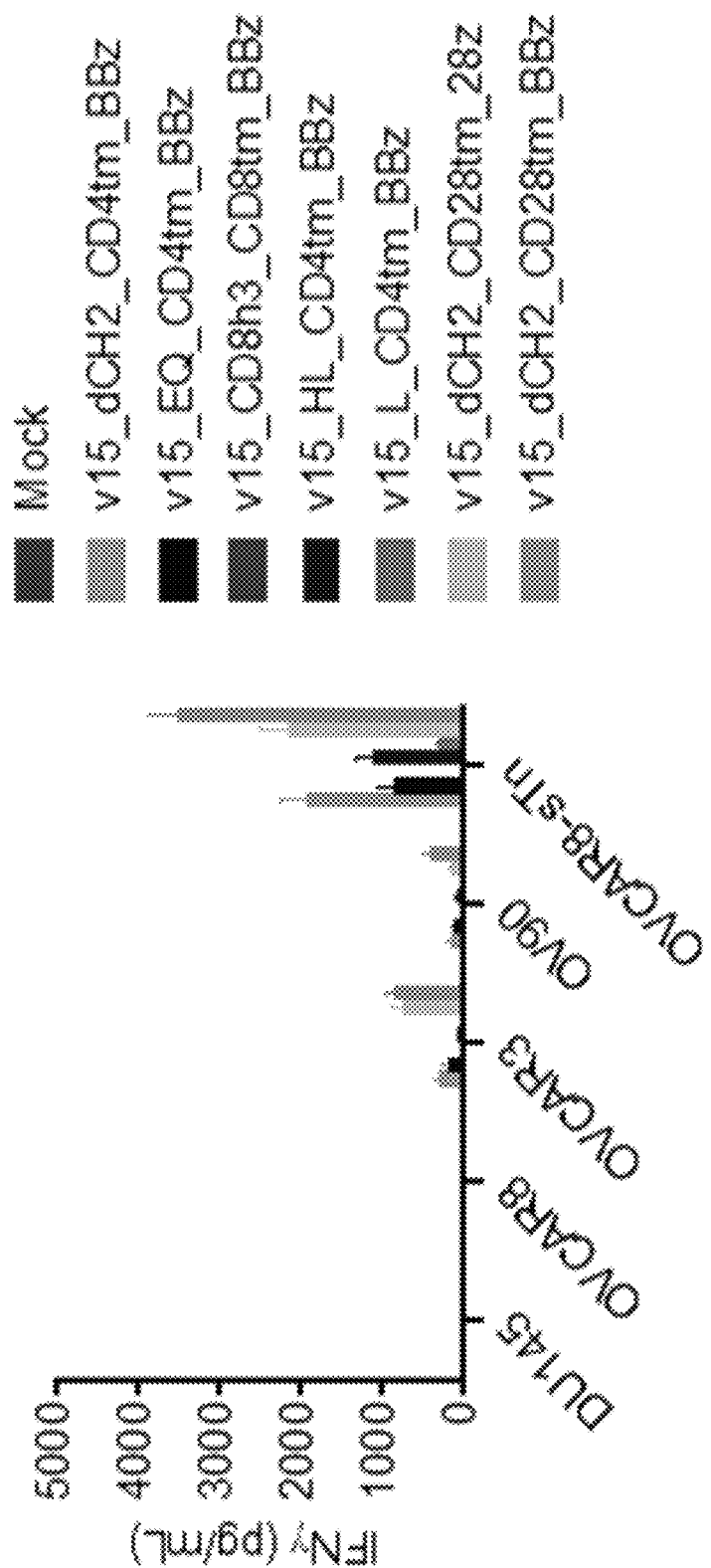
FIG. 17 shows varying humanized V15-CAR design impacts in vitro cytokine production of TAG72-CAR T cells. In vitro IFNγ production (24 hours), of CAR T cells against TAG72-negative (DU145, OVCAR8), and TAG72-positive (OVCAR3, OV90, OVCAR8-sTn) expressing tumor cells.

Varying V15-CAR design also impacts in vitro cytokine production of TAG72-CAR T cells. In vitro IFNγ production (24 hours), of CAR T cells against TAG72-negative (DU145, OVCAR8), and TAG72-positive (OVCAR3, OV90, OVCAR8-sTn) expressing tumor cells. While CARs with a CD28tm-BBz construct shows similar anti-tumor activity compared with the CD4tm-BBz construct, the CD28tm confers greater cytokine production in some TAG72-positive tumor cells (FIG. 17).

Figure 18A:
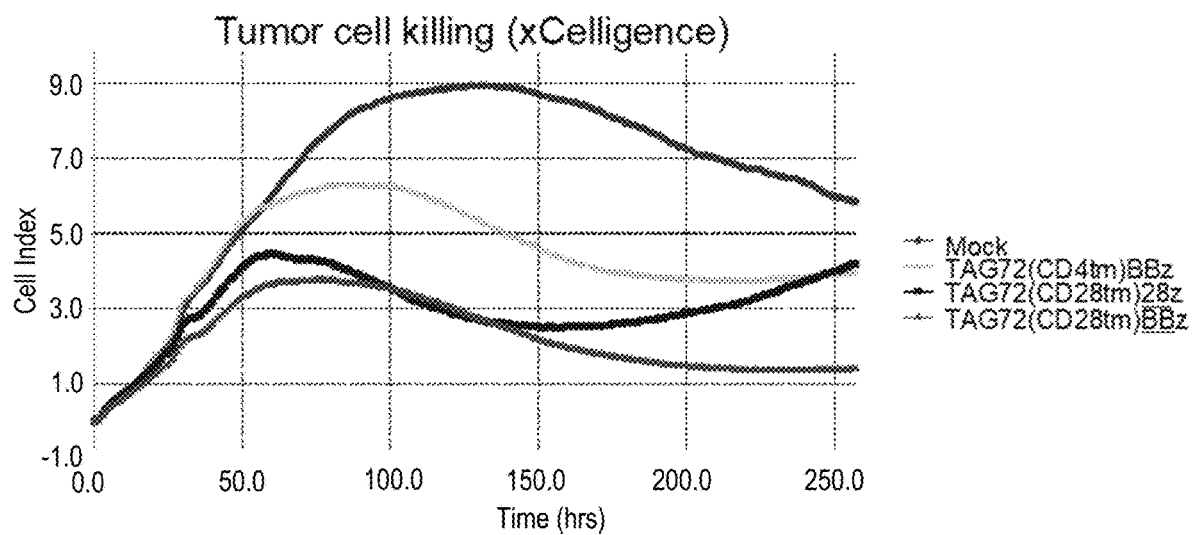
FIGS. 18A-18B show real-time long-term killing and proliferation of humanized TAG72 CAR T cells. (A) Real time cytotoxicity assay was performed using xCelligence technology with OV90 cells. The four T cells populations were plated at an effector to target ratio of 1-to-20 and observed for 10 days. Cell Index is indicative of live tumor count. (B) At endpoint, remaining cells were collected and analyzed by flow cytometry.
Figure 18B:
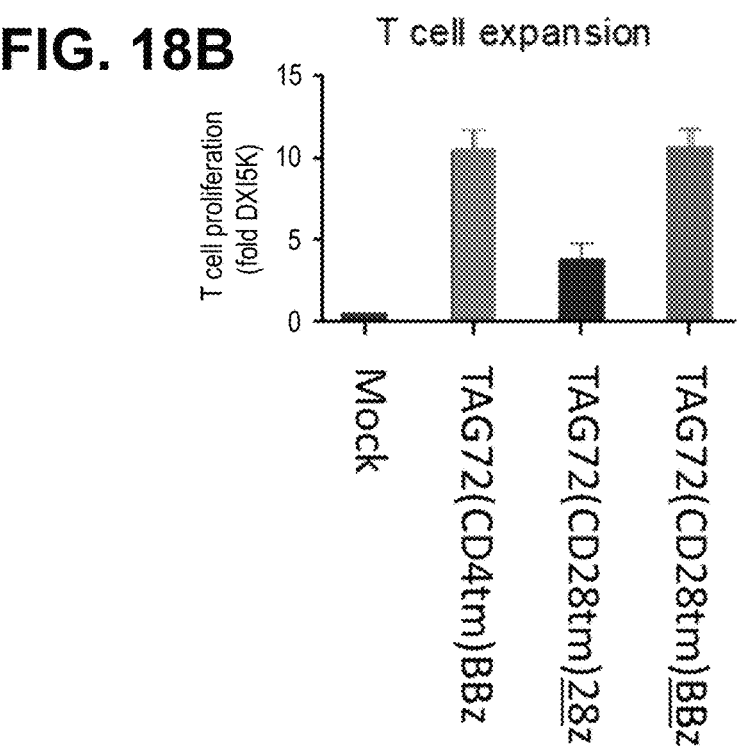

A real-time cytotoxicity assay was performed using xCelligence technology with OV90 cells and a few representative humanized TAG72-CAR T cells variants. The four T cells populations were plated at an effector to target ratio of 1-to-20 and observed for 10 days. Cell Index is indicative of live tumor count. All three representative humanized TAG72-CAR T cells variants demonstrated potent anti-tumor activity in this long-term killing assay (FIG. 18A). At the long-term killing assay endpoint, remaining cells were collected and analyzed by flow cytometry. T cell expansion was demonstrated for all three representative humanized TAG72-CAR T cells variants (FIG. 18B).

What is claimed is:

1. A nucleic acid molecule comprising a nucleotide sequence encoding a chimeric antigen receptor (CAR), wherein the CAR comprises: a scFv targeting Tag-72 comprising the amino acid sequence of SEQ ID NO: 33, a spacer, a CD4 or a CD28 transmembrane domain, a CD28 or 4-1BB co-stimulatory domain, and a CD3 ζ signaling domain.

2. The nucleic acid molecule of claim 1, wherein the transmembrane domain is a CD28 transmembrane domain.

3. The nucleic acid molecule of claim 2, wherein the CD28 transmembrane domain comprises the amino acid sequence of SEQ ID NO: 14.

4. The nucleic acid molecule of claim 2, wherein the CD28 transmembrane domain consists of the amino acid sequence of SEQ ID NO: 14.

5. The nucleic acid molecule of claim 1, wherein the transmembrane domain is a CD4 transmembrane domain.

6. The nucleic acid molecule of claim 5, wherein the CD4 transmembrane domain comprises the amino acid sequence of SEQ ID NO: 16.

7. The nucleic acid molecule of claim 5, wherein the CD4 transmembrane domain consists of the amino acid sequence of SEQ ID NO: 16.

8. The nucleic acid molecule of claim 1, wherein the spacer region comprises an amino acid sequence selected from the group consisting of the amino acid sequences of SEQ ID NOs: 2-12 and variants thereof having 1-5 amino acid substitutions.

9. The nucleic acid molecule of claim 1, wherein the spacer comprises an IgG hinge region.

10. The nucleic acid molecule of claim 1, wherein the spacer comprises 10-50 amino acids.

11. The nucleic acid molecule of claim 1, wherein the CD3ζ signaling domain comprises the amino acid sequence of SEQ ID NO:21.

12. An expression vector comprising the nucleic acid molecule of claim 1.

13. A viral vector comprising the nucleic acid molecule of claim 1.

14. A population of human T cells transduced by a vector comprising the nucleic acid molecule of claim 1.

15. The population of human T cells of claim 14, wherein the population of human T cells comprise central memory T cells.

16. The nucleic acid molecule of claim 1, wherein the spacer comprises an amino acid sequence selected from the group consisting of the amino acid sequences of SEQ ID NOs: 2-12.

17. The nucleic acid molecule of claim 1, wherein the co-stimulatory domain is a CD28 co-stimulatory domain.

18. The nucleic acid molecule of claim 17, wherein the CD28 co-stimulatory domain comprises the amino acid sequence of SEQ ID NO: 22 or 23.

19. The nucleic acid molecule of claim 1, wherein the co-stimulatory domain is a 4-1BB co-stimulatory domain.

20. The nucleic acid molecule of claim 19, wherein the 4-1BB co-stimulatory domain comprises the amino acid sequence of SEQ ID NO:24.

21. The nucleic acid molecule of claim 1, wherein the spacer comprises any one of the amino acid sequences of SEQ ID NO:2-12, the CD4 or a CD28 transmembrane domain comprises any one of the amino acid sequences of SEQ ID NO: 14-16, the CD28 or 4-1BB co-stimulatory domain comprises any one of the amino acid sequences of SEQ ID NO:22-24, and the CD3 ζ signaling domain comprises the amino acid sequence of SEQ ID NO:21.

22. The nucleic acid molecule of claim 1, wherein the CAR comprises the amino acid sequence of SEQ ID NO:36.

23. The nucleic acid molecule of claim 1, wherein the CAR consists of the amino acid sequence of SEQ ID NO:36.

24. A population of human T cells expressing a CAR, wherein the CAR comprises: a scFv targeting TAG-72 comprising the amino acid sequence of SEQ ID NO:33, a spacer, a CD4 or a CD28 transmembrane domain, a CD28 or 4-1BB co-stimulatory domain, and a CD3 ζ signaling domain.

25. The population of human T cells of claim 24, wherein the transmembrane domain is a CD28 transmembrane domain.

26. The population of human T cells of claim 25, wherein the CD28 transmembrane domain comprises the amino acid sequence of SEQ ID NO: 14.

27. The population of human T cells of claim 25, wherein the CD28 transmembrane domain consists of the amino acid sequence of SEQ ID NO: 14.

28. The population of human T cells of claim 24, wherein the transmembrane domain is a CD4 transmembrane domain.

29. The population of human T cells of claim 28, wherein the CD4 transmembrane domain comprises the amino acid sequence of SEQ ID NO: 16.

30. The population of human T cells of claim 28, wherein the CD4 transmembrane domain consists of the amino acid sequence of SEQ ID NO: 16.

31. The population of human T cells of claim 24, wherein the spacer region comprises an amino acid sequence selected from the group consisting of the amino acid sequences of SEQ ID NOs: 2-12 the variants thereof having 1-5 amino acid substitutions.

32. The population of human T cells of claim 24, wherein the spacer region comprises an amino acid sequence selected from the group consisting of the amino acid sequences of SEQ ID NOs: 2-12.

33. The population of human T cells of claim 24, wherein the spacer comprises an IgG hinge region.

34. The population of human T cells of claim 24, wherein the spacer comprises 10-50 amino acids.

35. The population of human T cells of claim 24, wherein the co-stimulatory domain is a CD28 co-stimulatory domain.

36. The population of human T cells of claim 35, wherein the CD28 co-stimulatory domain comprises the amino acid sequences of SEQ ID NO: 22 or 23.

37. The population of human T cells of claim 24, wherein the co-stimulatory domain is a 4-1BB co-stimulatory domain.

38. The population of human T cells of claim 37, wherein the 4-1BB co-stimulatory domain comprises the amino acid sequence of SEQ ID NO:24.

39. The population of human T cells of claim 24, wherein the CD3ζ signaling domain comprises the amino acid sequence of SEQ ID NO:21.

40. The population of human T cells of claim 24, wherein the spacer comprises any one of the amino acid sequences of SEQ ID NO: 2-12, the CD4 or a CD28 transmembrane domain comprises any one of the amino acid sequences of SEQ ID NO: 14-16, the CD28 or 4-1BB co-stimulatory domain comprises any one of the amino acid sequences of SEQ ID NO: 22-24, and the CD3 ζ signaling domain comprises the amino acid sequence of SEQ ID NO: 21.

41. The population of human T cells of claim 24, wherein the CAR comprises the amino acid sequence of SEQ ID NO:36.

42. The population of human T cells of claim 24, wherein the CAR consists of the amino acid sequence of SEQ ID NO:36.

* * * * *

SEQUENCE LISTING

<160> NUMBER OF SEQ ID NOS: 41

<210> SEQ ID NO 1
<211> LENGTH: 246
<212> TYPE: PRT
<213> ORGANISM: Homo sapiens

<400> SEQUENCE: 1

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Gly Ser Thr Ser Gly Gly Gly Ser Gly Gly Ser Gly
        115                 120                 125

Gly Gly Gly Ser Ser Asp Ile Val Met Ser Gln Ser Pro Asp Ser Leu
    130                 135                 140

Ala Val Ser Leu Gly Glu Arg Val Thr Leu Asn Cys Lys Ser Ser Gln
145                 150                 155                 160

Ser Leu Leu Tyr Ser Gly Asn Gln Lys Asn Tyr Leu Ala Trp Tyr Gln
                165                 170                 175

Gln Lys Pro Gly Gln Ser Pro Lys Leu Leu Ile Tyr Trp Ala Ser Ala
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Val Gln Ala Glu Asp Val Ala Val
    210                 215                 220

Tyr Tyr Cys Gln Gln Tyr Tyr Ser Tyr Pro Leu Thr Phe Gly Ala Gly
225                 230                 235                 240

Thr Lys Leu Glu Leu Lys
                245

<210> SEQ ID NO 2
<211> LENGTH: 10
<212> TYPE: PRT
<213> ORGANISM: Homo sapiens

<400> SEQUENCE: 2

Gly Gly Gly Ser Ser Gly Gly Gly Ser Gly
1               5                   10

<210> SEQ ID NO 3
<211> LENGTH: 12
<212> TYPE: PRT
<213> ORGANISM: Homo sapiens

<400> SEQUENCE: 3

Glu Ser Lys Tyr Gly Pro Pro Cys Pro Pro Cys Pro
1               5                   10

<210> SEQ ID NO 4
<211> LENGTH: 12
<212> TYPE: PRT
<213> ORGANISM: Homo sapiens

<400> SEQUENCE: 4

Glu Ser Lys Tyr Gly Pro Pro Cys Pro Ser Cys Pro
1               5                   10

<210> SEQ ID NO 5
<211> LENGTH: 22
<212> TYPE: PRT
<213> ORGANISM: Homo sapiens

<400> SEQUENCE: 5

Glu Ser Lys Tyr Gly Pro Pro Cys Pro Pro Cys Pro Gly Gly Gly Ser
1               5                   10                  15

Ser Gly Gly Gly Ser Gly
            20

<210> SEQ ID NO 6
<211> LENGTH: 39
<212> TYPE: PRT
<213> ORGANISM: Homo sapiens

<400> SEQUENCE: 6

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
            35

<210> SEQ ID NO 7
<211> LENGTH: 48
<212> TYPE: PRT
<213> ORGANISM: Homo sapiens

<400> SEQUENCE: 7

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
            35                  40                  45

<210> SEQ ID NO 8
<211> LENGTH: 45
<212> TYPE: PRT
<213> ORGANISM: Homo sapiens

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 9

```
<211> LENGTH: 129
<212> TYPE: PRT
<213> ORGANISM: Homo sapiens

<400> SEQUENCE: 9

Glu Ser Lys Tyr Gly Pro Pro Cys Pro Pro Cys Pro Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys

<210> SEQ ID NO 10
<211> LENGTH: 229
<212> TYPE: PRT
<213> ORGANISM: Homo sapiens

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205
```

Val Met His Glu Ala Leu His Asn His Tyr Thr Gln Lys Ser Leu Ser
    210                 215                 220

Leu Ser Leu Gly Lys
225

<210> SEQ ID NO 11
<211> LENGTH: 229
<212> TYPE: PRT
<213> ORGANISM: Homo sapiens

<400> SEQUENCE: 11

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Homo sapiens

<400> SEQUENCE: 13

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 14
<211> LENGTH: 27
<212> TYPE: PRT
<213> ORGANISM: Homo sapiens

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 15
<211> LENGTH: 28
<212> TYPE: PRT
<213> ORGANISM: Homo sapiens

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 16
<211> LENGTH: 22
<212> TYPE: PRT
<213> ORGANISM: Homo sapiens

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 17
<211> LENGTH: 21
<212> TYPE: PRT
<213> ORGANISM: Homo sapiens

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20

```
<210> SEQ ID NO 18
<211> LENGTH: 23
<212> TYPE: PRT
<213> ORGANISM: Homo sapiens

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 19
<211> LENGTH: 24
<212> TYPE: PRT
<213> ORGANISM: Homo sapiens

<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 20
<211> LENGTH: 27
<212> TYPE: PRT
<213> ORGANISM: Homo sapiens

<400> SEQUENCE: 20

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 21
<211> LENGTH: 112
<212> TYPE: PRT
<213> ORGANISM: Homo sapiens

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 22
<211> LENGTH: 41
<212> TYPE: PRT
<213> ORGANISM: Homo sapiens

<400> SEQUENCE: 22
```

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
        35                  40

<210> SEQ ID NO 23
<211> LENGTH: 41
<212> TYPE: PRT
<213> ORGANISM: Homo sapiens

<400> SEQUENCE: 23

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
        35                  40

<210> SEQ ID NO 24
<211> LENGTH: 42
<212> TYPE: PRT
<213> ORGANISM: Homo sapiens

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40

<210> SEQ ID NO 25
<211> LENGTH: 42
<212> TYPE: PRT
<213> ORGANISM: Homo sapiens

<400> SEQUENCE: 25

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
                20                  25                  30

Ala Asp Ala His Ser Thr Leu Ala Lys Ile
        35                  40

<210> SEQ ID NO 26
<211> LENGTH: 923
<212> TYPE: PRT
<213> ORGANISM: Homo sapiens

<400> SEQUENCE: 26

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
                20                  25                  30

Val Val Lys Pro Gly Ala Ser Val Lys Ile Ser Cys Lys Ala Ser Gly
            35                  40                  45

Tyr Thr Phe Thr Asp His Ala Ile His Trp Val Lys Gln Asn Pro Gly
        50                  55                  60
```

```
Gln Arg Leu Glu Trp Ile Gly Tyr Phe Ser Pro Gly Asn Asp Asp Phe
 65                  70                  75                  80
Lys Tyr Asn Glu Arg Phe Lys Gly Lys Ala Thr Leu Thr Ala Asp Thr
                 85                  90                  95
Ser Ala Ser Thr Ala Tyr Val Glu Leu Ser Ser Leu Arg Ser Glu Asp
            100                 105                 110
Thr Ala Val Tyr Phe Cys Thr Arg Ser Leu Asn Met Ala Tyr Trp Gly
        115                 120                 125
Gln Gly Thr Leu Val Thr Val Ser Ser Gly Ser Thr Ser Gly Gly Gly
    130                 135                 140
Ser Gly Gly Gly Ser Gly Gly Gly Ser Ser Asp Ile Val Met Ser
145                 150                 155                 160
Gln Ser Pro Asp Ser Leu Ala Val Ser Leu Gly Glu Arg Val Thr Leu
                165                 170                 175
Asn Cys Lys Ser Ser Gln Ser Leu Leu Tyr Ser Gly Asn Gln Lys Asn
            180                 185                 190
Tyr Leu Ala Trp Tyr Gln Gln Lys Pro Gly Gln Ser Pro Lys Leu Leu
        195                 200                 205
Ile Tyr Trp Ala Ser Ala Arg Glu Ser Gly Val Pro Asp Arg Phe Ser
    210                 215                 220
Gly Ser Gly Ser Gly Thr Asp Phe Thr Leu Thr Ile Ser Ser Val Gln
225                 230                 235                 240
Ala Glu Asp Val Ala Val Tyr Tyr Cys Gln Gln Tyr Tyr Ser Tyr Pro
                245                 250                 255
Leu Thr Phe Gly Ala Gly Thr Lys Leu Glu Leu Lys Glu Ser Lys Tyr
            260                 265                 270
Gly Pro Pro Cys Pro Pro Cys Pro Gly Gly Gly Ser Ser Gly Gly Gly
        275                 280                 285
Ser Gly Gly Gln Pro Arg Glu Pro Gln Val Tyr Thr Leu Pro Pro Ser
    290                 295                 300
Gln Glu Glu Met Thr Lys Asn Gln Val Ser Leu Thr Cys Leu Val Lys
305                 310                 315                 320
Gly Phe Tyr Pro Ser Asp Ile Ala Val Glu Trp Glu Ser Asn Gly Gln
                325                 330                 335
Pro Glu Asn Asn Tyr Lys Thr Thr Pro Pro Val Leu Asp Ser Asp Gly
            340                 345                 350
Ser Phe Phe Leu Tyr Ser Arg Leu Thr Val Asp Lys Ser Arg Trp Gln
        355                 360                 365
Glu Gly Asn Val Phe Ser Cys Ser Val Met His Glu Ala Leu His Asn
    370                 375                 380
His Tyr Thr Gln Lys Ser Leu Ser Leu Ser Leu Gly Lys Met Ala Leu
385                 390                 395                 400
Ile Val Leu Gly Gly Val Ala Gly Leu Leu Leu Phe Ile Gly Leu Gly
                405                 410                 415
Ile Phe Phe Lys Arg Gly Arg Lys Lys Leu Leu Tyr Ile Phe Lys Gln
            420                 425                 430
Pro Phe Met Arg Pro Val Gln Thr Thr Gln Glu Glu Asp Gly Cys Ser
        435                 440                 445
Cys Arg Phe Pro Glu Glu Glu Glu Gly Gly Cys Glu Leu Gly Gly Gly
    450                 455                 460
Arg Val Lys Phe Ser Arg Ser Ala Asp Ala Pro Ala Tyr Gln Gln Gly
465                 470                 475                 480
```

-continued

```
Gln Asn Gln Leu Tyr Asn Glu Leu Asn Leu Gly Arg Arg Glu Glu Tyr
                485                 490                 495
Asp Val Leu Asp Lys Arg Arg Gly Arg Asp Pro Glu Met Gly Gly Lys
            500                 505                 510
Pro Arg Arg Lys Asn Pro Gln Glu Gly Leu Tyr Asn Glu Leu Gln Lys
        515                 520                 525
Asp Lys Met Ala Glu Ala Tyr Ser Glu Ile Gly Met Lys Gly Glu Arg
    530                 535                 540
Arg Arg Gly Lys Gly His Asp Gly Leu Tyr Gln Gly Leu Ser Thr Ala
545                 550                 555                 560
Thr Lys Asp Thr Tyr Asp Ala Leu His Met Gln Ala Leu Pro Pro Arg
                565                 570                 575
Leu Glu Gly Gly Gly Glu Gly Arg Gly Ser Leu Leu Thr Cys Gly Asp
            580                 585                 590
Val Glu Glu Asn Pro Gly Pro Arg Met Pro Pro Arg Leu Leu Phe
        595                 600                 605
Phe Leu Leu Phe Leu Thr Pro Met Glu Val Arg Pro Glu Glu Pro Leu
    610                 615                 620
Val Val Lys Val Glu Glu Gly Asp Asn Ala Val Leu Gln Cys Leu Lys
625                 630                 635                 640
Gly Thr Ser Asp Gly Pro Thr Gln Gln Leu Thr Trp Ser Arg Glu Ser
                645                 650                 655
Pro Leu Lys Pro Phe Leu Lys Leu Ser Leu Gly Leu Pro Gly Leu Gly
            660                 665                 670
Ile His Met Arg Pro Leu Ala Ile Trp Leu Phe Ile Phe Asn Val Ser
        675                 680                 685
Gln Gln Met Gly Gly Phe Tyr Leu Cys Gln Pro Gly Pro Pro Ser Glu
    690                 695                 700
Lys Ala Trp Gln Pro Gly Trp Thr Val Asn Val Glu Gly Ser Gly Glu
705                 710                 715                 720
Leu Phe Arg Trp Asn Val Ser Asp Leu Gly Gly Leu Gly Cys Gly Leu
                725                 730                 735
Lys Asn Arg Ser Ser Glu Gly Pro Ser Ser Pro Ser Gly Lys Leu Met
            740                 745                 750
Ser Pro Lys Leu Tyr Val Trp Ala Lys Asp Arg Pro Glu Ile Trp Glu
        755                 760                 765
Gly Glu Pro Pro Cys Val Pro Pro Arg Asp Ser Leu Asn Gln Ser Leu
    770                 775                 780
Ser Gln Asp Leu Thr Met Ala Pro Gly Ser Thr Leu Trp Leu Ser Cys
785                 790                 795                 800
Gly Val Pro Pro Asp Ser Val Ser Arg Gly Pro Leu Ser Trp Thr His
                805                 810                 815
Val His Pro Lys Gly Pro Lys Ser Leu Leu Ser Leu Glu Leu Lys Asp
            820                 825                 830
Asp Arg Pro Ala Arg Asp Met Trp Val Met Glu Thr Gly Leu Leu Leu
        835                 840                 845
Pro Arg Ala Thr Ala Gln Asp Ala Gly Lys Tyr Tyr Cys His Arg Gly
    850                 855                 860
Asn Leu Thr Met Ser Phe His Leu Glu Ile Thr Ala Arg Pro Val Leu
865                 870                 875                 880
Trp His Trp Leu Leu Arg Thr Gly Gly Trp Lys Val Ser Ala Val Thr
                885                 890                 895
Leu Ala Tyr Leu Ile Phe Cys Leu Cys Ser Leu Val Gly Ile Leu His
```

```
                  900                 905                 910
Leu Gln Arg Ala Leu Val Leu Arg Arg Lys Arg
            915                 920

<210> SEQ ID NO 27
<211> LENGTH: 24
<212> TYPE: PRT
<213> ORGANISM: Homo sapiens

<400> SEQUENCE: 27

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 28
<211> LENGTH: 354
<212> TYPE: PRT
<213> ORGANISM: Homo sapiens

<400> SEQUENCE: 28

Leu Val Thr Ser Leu Leu Leu Cys Glu Leu Pro His Pro Ala Phe Leu
1               5                   10                  15

Leu Ile Pro Arg Lys Val Cys Asn Gly Ile Gly Ile Gly Glu Phe Lys
            20                  25                  30

Asp Ser Leu Ser Ile Asn Ala Thr Asn Ile Lys His Phe Lys Asn Cys
        35                  40                  45

Thr Ser Ile Ser Gly Asp Leu His Ile Leu Pro Val Ala Phe Arg Gly
    50                  55                  60

Asp Ser Phe Thr His Thr Pro Pro Leu Asp Pro Gln Glu Leu Asp Ile
65                  70                  75                  80

Leu Lys Thr Val Lys Glu Ile Thr Gly Phe Leu Leu Ile Gln Ala Trp
                85                  90                  95

Pro Glu Asn Arg Thr Asp Leu His Ala Phe Glu Asn Leu Glu Ile Ile
            100                 105                 110

Arg Gly Arg Thr Lys Gln His Gly Gln Phe Ser Leu Ala Val Val Ser
        115                 120                 125

Leu Asn Ile Thr Ser Leu Gly Leu Arg Ser Leu Lys Glu Ile Ser Asp
    130                 135                 140

Gly Asp Val Ile Ile Ser Gly Asn Lys Asn Leu Cys Tyr Ala Asn Thr
145                 150                 155                 160

Ile Asn Trp Lys Lys Leu Phe Gly Thr Ser Gly Gln Lys Thr Lys Ile
                165                 170                 175

Ile Ser Asn Arg Gly Glu Asn Ser Cys Lys Ala Thr Gly Gln Val Cys
            180                 185                 190

His Ala Leu Cys Ser Pro Glu Gly Cys Trp Gly Pro Glu Pro Arg Asp
        195                 200                 205

Cys Val Ser Cys Arg Asn Val Ser Arg Gly Arg Glu Cys Val Asp Lys
    210                 215                 220

Cys Asn Leu Leu Glu Gly Glu Pro Arg Glu Phe Val Glu Asn Ser Glu
225                 230                 235                 240

Cys Ile Gln Cys His Pro Glu Cys Leu Pro Gln Ala Met Asn Ile Thr
                245                 250                 255

Cys Thr Gly Arg Gly Pro Asp Asn Cys Ile Gln Cys Ala His Tyr Ile
            260                 265                 270

Asp Gly Pro His Cys Val Lys Thr Cys Pro Ala Gly Val Met Gly Glu
```

```
                    275                 280                 285
Asn Asn Thr Leu Val Trp Lys Tyr Ala Asp Ala Gly His Val Cys His
    290                 295                 300

Leu Cys His Pro Asn Cys Thr Tyr Gly Cys Thr Gly Pro Gly Leu Glu
305                 310                 315                 320

Gly Cys Pro Thr Asn Gly Pro Lys Ile Pro Ser Ile Ala Thr Gly Met
                    325                 330                 335

Val Gly Ala Leu Leu Leu Leu Val Val Ala Leu Gly Ile Gly Leu
                340                 345                 350

Phe Met

<210> SEQ ID NO 29
<211> LENGTH: 576
<212> TYPE: PRT
<213> ORGANISM: Homo sapiens

<400> SEQUENCE: 29

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
                20                  25                  30

Val Val Lys Pro Gly Ala Ser Val Lys Ile Ser Cys Lys Ala Ser Gly
            35                  40                  45

Tyr Thr Phe Thr Asp His Ala Ile His Trp Val Lys Gln Asn Pro Gly
        50                  55                  60

Gln Arg Leu Glu Trp Ile Gly Tyr Phe Ser Pro Gly Asn Asp Asp Phe
65                  70                  75                  80

Lys Tyr Asn Glu Arg Phe Lys Gly Lys Ala Thr Leu Thr Ala Asp Thr
                85                  90                  95

Ser Ala Ser Thr Ala Tyr Val Glu Leu Ser Ser Leu Arg Ser Glu Asp
            100                 105                 110

Thr Ala Val Tyr Phe Cys Thr Arg Ser Leu Asn Met Ala Tyr Trp Gly
        115                 120                 125

Gln Gly Thr Leu Val Thr Val Ser Ser Gly Ser Thr Ser Gly Gly Gly
    130                 135                 140

Ser Gly Gly Gly Ser Gly Gly Gly Ser Ser Asp Ile Val Met Ser
145                 150                 155                 160

Gln Ser Pro Asp Ser Leu Ala Val Ser Leu Gly Glu Arg Val Thr Leu
                165                 170                 175

Asn Cys Lys Ser Ser Gln Ser Leu Leu Tyr Ser Gly Asn Gln Lys Asn
            180                 185                 190

Tyr Leu Ala Trp Tyr Gln Gln Lys Pro Gly Gln Ser Pro Lys Leu Leu
        195                 200                 205

Ile Tyr Trp Ala Ser Ala Arg Glu Ser Gly Val Pro Asp Arg Phe Ser
    210                 215                 220

Gly Ser Gly Ser Gly Thr Asp Phe Thr Leu Thr Ile Ser Ser Val Gln
225                 230                 235                 240

Ala Glu Asp Val Ala Val Tyr Tyr Cys Gln Gln Tyr Tyr Ser Tyr Pro
                245                 250                 255

Leu Thr Phe Gly Ala Gly Thr Lys Leu Glu Leu Lys Glu Ser Lys Tyr
            260                 265                 270

Gly Pro Pro Cys Pro Pro Cys Pro Gly Gly Ser Ser Gly Gly Gly
        275                 280                 285

Ser Gly Gly Gln Pro Arg Glu Pro Gln Val Tyr Thr Leu Pro Pro Ser
```

```
            290                 295                 300
Gln Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Arg Leu Thr Val Asp Lys Ser Arg Trp Gln
        355                 360                 365

Glu Gly Asn Val Phe Ser Cys Ser Val Met His Glu Ala Leu His Asn
370                 375                 380

His Tyr Thr Gln Lys Ser Leu Ser Leu Ser Leu Gly Lys Met Ala Leu
385                 390                 395                 400

Ile Val Leu Gly Gly Val Ala Gly Leu Leu Leu Phe Ile Gly Leu Gly
                405                 410                 415

Ile Phe Phe Lys Arg Gly Arg Lys Lys Leu Leu Tyr Ile Phe Lys Gln
            420                 425                 430

Pro Phe Met Arg Pro Val Gln Thr Thr Gln Glu Glu Asp Gly Cys Ser
        435                 440                 445

Cys Arg Phe Pro Glu Glu Glu Glu Gly Gly Cys Glu Leu Gly Gly Gly
450                 455                 460

Arg Val Lys Phe Ser Arg Ser Ala Asp Ala Pro Ala Tyr Gln Gln Gly
465                 470                 475                 480

Gln Asn Gln Leu Tyr Asn Glu Leu Asn Leu Gly Arg Arg Glu Glu Tyr
                485                 490                 495

Asp Val Leu Asp Lys Arg Arg Gly Arg Asp Pro Glu Met Gly Gly Lys
            500                 505                 510

Pro Arg Arg Lys Asn Pro Gln Glu Gly Leu Tyr Asn Glu Leu Gln Lys
        515                 520                 525

Asp Lys Met Ala Glu Ala Tyr Ser Glu Ile Gly Met Lys Gly Glu Arg
530                 535                 540

Arg Arg Gly Lys Gly His Asp Gly Leu Tyr Gln Gly Leu Ser Thr Ala
545                 550                 555                 560

Thr Lys Asp Thr Tyr Asp Ala Leu His Met Gln Ala Leu Pro Pro Arg
                565                 570                 575

<210> SEQ ID NO 30
<211> LENGTH: 576
<212> TYPE: PRT
<213> ORGANISM: Homo sapiens

<400> SEQUENCE: 30

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
                20                  25                  30

Val Val Lys Pro Gly Ala Ser Val Lys Ile Ser Cys Lys Ala Ser Gly
            35                  40                  45

Tyr Thr Phe Thr Asp His Ala Ile His Trp Val Lys Gln Asn Pro Gly
        50                  55                  60

Gln Arg Leu Glu Trp Ile Gly Tyr Phe Ser Pro Gly Asn Asp Asp Phe
65                  70                  75                  80

Lys Tyr Asn Glu Arg Phe Lys Gly Lys Ala Thr Leu Thr Ala Asp Thr
                85                  90                  95
```

-continued

Ser Ala Ser Thr Ala Tyr Val Glu Leu Ser Ser Leu Arg Ser Glu Asp
                100                 105                 110

Thr Ala Val Tyr Phe Cys Thr Arg Ser Leu Asn Met Ala Tyr Trp Gly
            115                 120                 125

Gln Gly Thr Leu Val Thr Val Ser Ser Gly Ser Thr Ser Gly Gly Gly
        130                 135                 140

Ser Gly Gly Gly Ser Gly Gly Gly Ser Ser Asp Ile Val Met Ser
145                 150                 155                 160

Gln Ser Pro Asp Ser Leu Ala Val Ser Leu Gly Glu Arg Val Thr Leu
                165                 170                 175

Asn Cys Lys Ser Ser Gln Ser Leu Leu Tyr Ser Gly Asn Gln Lys Asn
            180                 185                 190

Tyr Leu Ala Trp Tyr Gln Gln Lys Pro Gly Gln Ser Pro Lys Leu Leu
        195                 200                 205

Ile Tyr Trp Ala Ser Ala Arg Glu Ser Gly Val Pro Asp Arg Phe Ser
    210                 215                 220

Gly Ser Gly Ser Gly Thr Asp Phe Thr Leu Thr Ile Ser Ser Val Gln
225                 230                 235                 240

Ala Glu Asp Val Ala Val Tyr Tyr Cys Gln Gln Tyr Tyr Ser Tyr Pro
                245                 250                 255

Leu Thr Phe Gly Ala Gly Thr Lys Leu Glu Leu Lys Glu Ser Lys Tyr
            260                 265                 270

Gly Pro Pro Cys Pro Pro Cys Pro Gly Gly Gly Ser Ser Gly Gly Gly
        275                 280                 285

Ser Gly Gly Gln Pro Arg Glu Pro Gln Val Tyr Thr Leu Pro Pro Ser
    290                 295                 300

Gln Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Arg Leu Thr Val Asp Lys Ser Arg Trp Gln
        355                 360                 365

Glu Gly Asn Val Phe Ser Cys Ser Val Met His Glu Ala Leu His Asn
    370                 375                 380

His Tyr Thr Gln Lys Ser Leu Ser Leu Ser Leu Gly Lys Met Ala Leu
385                 390                 395                 400

Ile Val Leu Gly Gly Val Ala Gly Leu Leu Leu Phe Ile Gly Leu Gly
                405                 410                 415

Ile Phe Phe Lys Arg Gly Arg Lys Lys Leu Leu Tyr Ile Phe Lys Gln
            420                 425                 430

Pro Phe Met Arg Pro Val Gln Thr Thr Gln Glu Glu Asp Gly Cys Ser
        435                 440                 445

Cys Arg Phe Pro Glu Glu Glu Glu Gly Gly Cys Glu Leu Gly Gly Gly
    450                 455                 460

Arg Val Lys Phe Ser Arg Ser Ala Asp Ala Pro Ala Tyr Gln Gln Gly
465                 470                 475                 480

Gln Asn Gln Leu Tyr Asn Glu Leu Asn Leu Gly Arg Arg Glu Glu Tyr
                485                 490                 495

Asp Val Leu Asp Lys Arg Arg Gly Arg Asp Pro Glu Met Gly Gly Lys
            500                 505                 510

Pro Arg Arg Lys Asn Pro Gln Glu Gly Leu Tyr Asn Glu Leu Gln Lys

```
                515                 520                 525
Asp Lys Met Ala Glu Ala Tyr Ser Glu Ile Gly Met Lys Gly Glu Arg
530                 535                 540

Arg Arg Gly Lys Gly His Asp Gly Leu Tyr Gln Gly Leu Ser Thr Ala
545                 550                 555                 560

Thr Lys Asp Thr Tyr Asp Ala Leu His Met Gln Ala Leu Pro Pro Arg
                565                 570                 575

<210> SEQ ID NO 31
<211> LENGTH: 576
<212> TYPE: PRT
<213> ORGANISM: Homo sapiens

<400> SEQUENCE: 31

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
                20                  25                  30

Val Val Lys Pro Gly Ala Ser Val Lys Ile Ser Cys Lys Ala Ser Gly
            35                  40                  45

Tyr Thr Phe Thr Asp His Ala Ile His Trp Val Lys Gln Asn Pro Gly
        50                  55                  60

Gln Arg Leu Glu Trp Ile Gly Tyr Phe Ser Pro Gly Asn Asp Asp Phe
65                  70                  75                  80

Lys Tyr Ser Gln Lys Phe Gln Gly Lys Ala Thr Leu Thr Ala Asp Thr
                85                  90                  95

Ser Ala Ser Thr Ala Tyr Val Glu Leu Ser Ser Leu Arg Ser Glu Asp
            100                 105                 110

Thr Ala Val Tyr Phe Cys Thr Arg Ser Leu Asn Met Ala Tyr Trp Gly
        115                 120                 125

Gln Gly Thr Leu Val Thr Val Ser Ser Gly Ser Thr Ser Gly Gly Gly
        130                 135                 140

Ser Gly Gly Gly Ser Gly Gly Gly Ser Ser Asp Ile Val Met Ser
145                 150                 155                 160

Gln Ser Pro Asp Ser Leu Ala Val Ser Leu Gly Glu Arg Val Thr Leu
                165                 170                 175

Asn Cys Lys Ser Ser Gln Ser Val Leu Tyr Ser Ser Asn Ser Lys Asn
            180                 185                 190

Tyr Leu Ala Trp Tyr Gln Gln Lys Pro Gly Gln Ser Pro Lys Leu Leu
        195                 200                 205

Ile Tyr Trp Ala Ser Thr Arg Glu Ser Gly Val Pro Asp Arg Phe Ser
        210                 215                 220

Gly Ser Gly Ser Gly Thr Asp Phe Thr Leu Thr Ile Ser Ser Val Gln
225                 230                 235                 240

Ala Glu Asp Val Ala Val Tyr Tyr Cys Gln Gln Tyr Tyr Ser Tyr Pro
                245                 250                 255

Leu Ser Phe Gly Ala Gly Thr Lys Leu Glu Leu Lys Glu Ser Lys Tyr
            260                 265                 270

Gly Pro Pro Cys Pro Pro Cys Pro Gly Gly Gly Ser Ser Gly Gly Gly
        275                 280                 285

Ser Gly Gly Gln Pro Arg Glu Pro Gln Val Tyr Thr Leu Pro Pro Ser
        290                 295                 300

Gln Glu Glu Met Thr Lys Asn Gln Val Ser Leu Thr Cys Leu Val Lys
305                 310                 315                 320
```

```
Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Arg Leu Thr Val Asp Lys Ser Arg Trp Gln
        355                 360                 365

Glu Gly Asn Val Phe Ser Cys Ser Val Met His Glu Ala Leu His Asn
    370                 375                 380

His Tyr Thr Gln Lys Ser Leu Ser Leu Ser Leu Gly Lys Met Ala Leu
385                 390                 395                 400

Ile Val Leu Gly Gly Val Ala Gly Leu Leu Leu Phe Ile Gly Leu Gly
                405                 410                 415

Ile Phe Phe Lys Arg Gly Arg Lys Lys Leu Leu Tyr Ile Phe Lys Gln
                420                 425                 430

Pro Phe Met Arg Pro Val Gln Thr Thr Gln Glu Glu Asp Gly Cys Ser
            435                 440                 445

Cys Arg Phe Pro Glu Glu Glu Glu Gly Gly Cys Glu Leu Gly Gly Gly
        450                 455                 460

Arg Val Lys Phe Ser Arg Ser Ala Asp Ala Pro Ala Tyr Gln Gln Gly
465                 470                 475                 480

Gln Asn Gln Leu Tyr Asn Glu Leu Asn Leu Gly Arg Arg Glu Glu Tyr
                485                 490                 495

Asp Val Leu Asp Lys Arg Arg Gly Arg Asp Pro Glu Met Gly Gly Lys
                500                 505                 510

Pro Arg Arg Lys Asn Pro Gln Glu Gly Leu Tyr Asn Glu Leu Gln Lys
            515                 520                 525

Asp Lys Met Ala Glu Ala Tyr Ser Glu Ile Gly Met Lys Gly Glu Arg
        530                 535                 540

Arg Arg Gly Lys Gly His Asp Gly Leu Tyr Gln Gly Leu Ser Thr Ala
545                 550                 555                 560

Thr Lys Asp Thr Tyr Asp Ala Leu His Met Gln Ala Leu Pro Pro Arg
                565                 570                 575

<210> SEQ ID NO 32
<211> LENGTH: 576
<212> TYPE: PRT
<213> ORGANISM: Homo sapiens

<400> SEQUENCE: 32

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr Asp His Ala Ile His Trp Val Arg Gln Ala Pro Gly
        50                  55                  60

Gln Arg Leu Glu Trp Met Gly Tyr Phe Ser Pro Gly Asn Asp Asp Phe
65                  70                  75                  80

Lys Tyr Ser Gln Lys Phe Gln Gly Arg Val Thr Ile Thr Ala Asp Thr
                85                  90                  95

Ser Ala Ser Thr Ala Tyr Met Glu Leu Ser Ser Leu Arg Ser Glu Asp
            100                 105                 110

Thr Ala Val Tyr Phe Cys Thr Arg Ser Leu Asn Met Ala Tyr Trp Gly
        115                 120                 125
```

-continued

```
Gln Gly Thr Leu Val Thr Val Ser Ser Gly Ser Gly Gly Gly
    130                 135                 140

Ser Gly Gly Gly Ser Gly Gly Gly Ser Ser Asp Ile Val Met Thr
145                 150                 155                 160

Gln Ser Pro Asp Ser Leu Ala Val Ser Leu Gly Glu Arg Ala Thr Ile
                165                 170                 175

Asn Cys Lys Ser Ser Gln Ser Leu Leu Tyr Ser Ser Asn Ser Lys Asn
                180                 185                 190

Tyr Leu Ala Trp Tyr Gln Gln Lys Pro Gly Gln Pro Pro Lys Leu Leu
            195                 200                 205

Ile Tyr Trp Ala Ser Thr Arg Glu Ser Gly Val Pro Asp Arg Phe Ser
    210                 215                 220

Gly Ser Gly Ser Gly Thr Asp Phe Thr Leu Thr Ile Ser Ser Leu Gln
225                 230                 235                 240

Ala Glu Asp Val Ala Val Tyr Tyr Cys Gln Gln Pro Tyr Ser Tyr Pro
                245                 250                 255

Leu Ser Phe Gly Ala Gly Thr Lys Leu Glu Leu Lys Glu Ser Lys Tyr
                260                 265                 270

Gly Pro Pro Cys Pro Pro Cys Pro Gly Gly Ser Ser Gly Gly Gly
            275                 280                 285

Ser Gly Gly Gln Pro Arg Glu Pro Gln Val Tyr Thr Leu Pro Pro Ser
    290                 295                 300

Gln Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Arg Leu Thr Val Asp Lys Ser Arg Trp Gln
    355                 360                 365

Glu Gly Asn Val Phe Ser Cys Ser Val Met His Glu Ala Leu His Asn
370                 375                 380

His Tyr Thr Gln Lys Ser Leu Ser Leu Ser Leu Gly Lys Met Ala Leu
385                 390                 395                 400

Ile Val Leu Gly Gly Val Ala Gly Leu Leu Phe Ile Gly Leu
                405                 410                 415

Ile Phe Phe Lys Arg Gly Arg Lys Lys Leu Leu Tyr Ile Phe Lys Gln
                420                 425                 430

Pro Phe Met Arg Pro Val Gln Thr Thr Gln Glu Glu Asp Gly Cys Ser
            435                 440                 445

Cys Arg Phe Pro Glu Glu Glu Gly Gly Cys Glu Leu Gly Gly Gly
    450                 455                 460

Arg Val Lys Phe Ser Arg Ser Ala Asp Ala Pro Ala Tyr Gln Gln Gly
465                 470                 475                 480

Gln Asn Gln Leu Tyr Asn Glu Leu Asn Leu Gly Arg Arg Glu Glu Tyr
                485                 490                 495

Asp Val Leu Asp Lys Arg Arg Gly Arg Asp Pro Glu Met Gly Gly Lys
                500                 505                 510

Pro Arg Arg Lys Asn Pro Gln Glu Gly Leu Tyr Asn Glu Leu Gln Lys
            515                 520                 525

Asp Lys Met Ala Glu Ala Tyr Ser Glu Ile Gly Met Lys Gly Glu Arg
530                 535                 540
```

Arg Arg Gly Lys Gly His Asp Gly Leu Tyr Gln Gly Leu Ser Thr Ala
545                 550                 555                 560

Thr Lys Asp Thr Tyr Asp Ala Leu His Met Gln Ala Leu Pro Pro Arg
                565                 570                 575

<210> SEQ ID NO 33
<211> LENGTH: 246
<212> TYPE: PRT
<213> ORGANISM: Homo sapiens

<400> SEQUENCE: 33

Gln Val Gln Leu Val Gln Ser Gly Ala Glu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Gly Gln Arg Leu Glu Trp Ile
            35                  40                  45

Gly Tyr Phe Ser Pro Gly Asn Asp Asp Phe Lys Tyr Ser Gln Lys Phe
    50                  55                  60

Gln Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Gly Ser Thr Ser Gly Gly Gly Ser Gly Gly Gly Ser Gly
        115                 120                 125

Gly Gly Gly Ser Ser Asp Ile Val Met Ser Gln Ser Pro Asp Ser Leu
    130                 135                 140

Ala Val Ser Leu Gly Glu Arg Val Thr Leu Asn Cys Lys Ser Ser Gln
145                 150                 155                 160

Ser Val Leu Tyr Ser Ser Asn Ser Lys Asn Tyr Leu Ala Trp Tyr Gln
                165                 170                 175

Gln Lys Pro Gly Gln Ser Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Val Gln Ala Glu Asp Val Ala Val
    210                 215                 220

Tyr Tyr Cys Gln Gln Tyr Tyr Ser Tyr Pro Leu Ser Phe Gly Ala Gly
225                 230                 235                 240

Thr Lys Leu Glu Leu Lys
                245

<210> SEQ ID NO 34
<211> LENGTH: 246
<212> TYPE: PRT
<213> ORGANISM: Homo sapiens

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Arg Leu Glu Trp Met
            35                  40                  45

```
Gly Tyr Phe Ser Pro Gly Asn Asp Asp Phe Lys Tyr Ser Gln Lys Phe
         50                  55                  60

Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Thr Arg Ser Leu Asn Met Ala Tyr Trp Gly Gln Gly Thr Leu Val Thr
            100                 105                 110

Val Ser Ser Gly Ser Thr Ser Gly Gly Gly Ser Gly Gly Gly Ser Gly
        115                 120                 125

Gly Gly Ser Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Leu Tyr Ser Ser Asn Ser Lys Asn Tyr Leu Ala Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
195                 200                 205

Asp Phe Thr Leu Thr Ile Ser Ser Leu Gln Ala Glu Asp Val Ala Val
            210                 215                 220

Tyr Tyr Cys Gln Gln Pro Tyr Ser Tyr Pro Leu Ser Phe Gly Ala Gly
225                 230                 235                 240

Thr Lys Leu Glu Leu Lys
            245

<210> SEQ ID NO 35
<211> LENGTH: 554
<212> TYPE: PRT
<213> ORGANISM: Homo sapiens

<400> SEQUENCE: 35

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
 65                 70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Gly Ser Thr Ser Gly Gly Gly Ser Gly Gly Gly Ser Gly
        115                 120                 125

Gly Gly Ser Ser Asp Ile Val Met Ser Gln Ser Pro Asp Ser Leu
    130                 135                 140

Ala Val Ser Leu Gly Glu Arg Val Thr Leu Asn Cys Lys Ser Ser Gln
145                 150                 155                 160

Ser Leu Leu Tyr Ser Gly Asn Gln Lys Asn Tyr Leu Ala Trp Tyr Gln
                165                 170                 175
```

Gln Lys Pro Gly Gln Ser Pro Lys Leu Leu Ile Tyr Trp Ala Ser Ala
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Val Gln Ala Glu Asp Val Ala Val
    210                 215                 220

Tyr Tyr Cys Gln Gln Tyr Tyr Ser Tyr Pro Leu Thr Phe Gly Ala Gly
225                 230                 235                 240

Thr Lys Leu Glu Leu Lys Glu Ser Lys Tyr Gly Pro Pro Cys Pro Pro
            245                 250                 255

Cys Pro Gly Gly Gly Ser Ser Gly Gly Ser Gly Gly Gln Pro Arg
        260                 265                 270

Glu Pro Gln Val Tyr Thr Leu Pro Pro Ser Gln Glu Glu Met Thr Lys
    275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
            325                 330                 335

Arg Leu Thr Val Asp Lys Ser Arg Trp Gln Glu Gly Asn Val Phe Ser
        340                 345                 350

Cys Ser Val Met His Glu Ala Leu His Asn His Tyr Thr Gln Lys Ser
    355                 360                 365

Leu Ser Leu Ser Leu Gly Lys Met Ala Leu Ile Val Leu Gly Gly Val
    370                 375                 380

Ala Gly Leu Leu Leu Phe Ile Gly Leu Gly Ile Phe Phe Lys Arg Gly
385                 390                 395                 400

Arg Lys Lys Leu Leu Tyr Ile Phe Lys Gln Pro Phe Met Arg Pro Val
            405                 410                 415

Gln Thr Thr Gln Glu Glu Asp Gly Cys Ser Cys Arg Phe Pro Glu Glu
        420                 425                 430

Glu Glu Gly Gly Cys Glu Leu Gly Gly Arg Val Lys Phe Ser Arg
    435                 440                 445

Ser Ala Asp Ala Pro Ala Tyr Gln Gln Gly Gln Asn Gln Leu Tyr Asn
450                 455                 460

Glu Leu Asn Leu Gly Arg Arg Glu Glu Tyr Asp Val Leu Asp Lys Arg
465                 470                 475                 480

Arg Gly Arg Asp Pro Glu Met Gly Gly Lys Pro Arg Arg Lys Asn Pro
            485                 490                 495

Gln Glu Gly Leu Tyr Asn Glu Leu Gln Lys Asp Lys Met Ala Glu Ala
        500                 505                 510

Tyr Ser Glu Ile Gly Met Lys Gly Glu Arg Arg Gly Lys Gly His
    515                 520                 525

Asp Gly Leu Tyr Gln Gly Leu Ser Thr Ala Thr Lys Asp Thr Tyr Asp
    530                 535                 540

Ala Leu His Met Gln Ala Leu Pro Pro Arg
545                 550

<210> SEQ ID NO 36
<211> LENGTH: 554
<212> TYPE: PRT
<213> ORGANISM: Homo sapiens

<400> SEQUENCE: 36

```
Gln Val Gln Leu Val Gln Ser Gly Ala Glu Val Lys Pro Gly Ala
1               5                   10                  15
Ser Val Lys Ile Ser Cys Lys Ala Ser Gly Tyr Thr Phe Thr Asp His
            20                  25                  30
Ala Ile His Trp Val Lys Gln Asn Pro Gly Gln Arg Leu Glu Trp Ile
        35                  40                  45
Gly Tyr Phe Ser Pro Gly Asn Asp Asp Phe Lys Tyr Asn Glu Arg Phe
    50                  55                  60
Lys Gly Lys Ala Thr Leu Thr Ala Asp Thr Ser Ala Ser Thr Ala Tyr
65                  70                  75                  80
Val Glu Leu Ser Ser Leu Arg Ser Glu Asp Thr Ala Val Tyr Phe Cys
                85                  90                  95
Thr Arg Ser Leu Asn Met Ala Tyr Trp Gly Gln Gly Thr Leu Val Thr
            100                 105                 110
Val Ser Ser Gly Ser Thr Ser Gly Gly Gly Ser Gly Gly Gly Ser Gly
        115                 120                 125
Gly Gly Ser Ser Asp Ile Val Met Ser Gln Ser Pro Asp Ser Leu
    130                 135                 140
Ala Val Ser Leu Gly Glu Arg Val Thr Leu Asn Cys Lys Ser Ser Gln
145                 150                 155                 160
Ser Leu Leu Tyr Ser Gly Asn Gln Lys Asn Tyr Leu Ala Trp Tyr Gln
                165                 170                 175
Gln Lys Pro Gly Gln Ser Pro Lys Leu Leu Ile Tyr Trp Ala Ser Ala
            180                 185                 190
Arg Glu Ser Gly Val Pro Asp Arg Phe Ser Gly Ser Gly Ser Gly Thr
        195                 200                 205
Asp Phe Thr Leu Thr Ile Ser Ser Val Gln Ala Glu Asp Val Ala Val
    210                 215                 220
Tyr Tyr Cys Gln Gln Tyr Tyr Ser Tyr Pro Leu Thr Phe Gly Ala Gly
225                 230                 235                 240
Thr Lys Leu Glu Leu Lys Glu Ser Lys Tyr Gly Pro Pro Cys Pro Pro
                245                 250                 255
Cys Pro Gly Gly Gly Ser Ser Gly Gly Gly Ser Gly Gly Gln Pro Arg
            260                 265                 270
Glu Pro Gln Val Tyr Thr Leu Pro Pro Ser Gln Glu Glu Met Thr Lys
        275                 280                 285
Asn Gln Val Ser Leu Thr Cys Leu Val Lys Gly Phe Tyr Pro Ser Asp
    290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Arg Leu Thr Val Asp Lys Ser Arg Trp Gln Glu Gly Asn Val Phe Ser
            340                 345                 350
Cys Ser Val Met His Glu Ala Leu His Asn His Tyr Thr Gln Lys Ser
        355                 360                 365
Leu Ser Leu Ser Leu Gly Lys Met Ala Leu Ile Val Leu Gly Gly Val
    370                 375                 380
Ala Gly Leu Leu Leu Phe Ile Gly Leu Gly Ile Phe Phe Lys Arg Gly
385                 390                 395                 400
Arg Lys Lys Leu Leu Tyr Ile Phe Lys Gln Pro Phe Met Arg Pro Val
                405                 410                 415
```

-continued

```
Gln Thr Thr Gln Glu Glu Asp Gly Cys Ser Cys Arg Phe Pro Glu Glu
                420                 425                 430

Glu Glu Gly Gly Cys Glu Leu Gly Gly Arg Val Lys Phe Ser Arg
            435                 440                 445

Ser Ala Asp Ala Pro Ala Tyr Gln Gln Gly Gln Asn Gln Leu Tyr Asn
450                 455                 460

Glu Leu Asn Leu Gly Arg Arg Glu Glu Tyr Asp Val Leu Asp Lys Arg
465                 470                 475                 480

Arg Gly Arg Asp Pro Glu Met Gly Gly Lys Pro Arg Arg Lys Asn Pro
                485                 490                 495

Gln Glu Gly Leu Tyr Asn Glu Leu Gln Lys Asp Lys Met Ala Glu Ala
            500                 505                 510

Tyr Ser Glu Ile Gly Met Lys Gly Glu Arg Arg Arg Gly Lys Gly His
                515                 520                 525

Asp Gly Leu Tyr Gln Gly Leu Ser Thr Ala Thr Lys Asp Thr Tyr Asp
530                 535                 540

Ala Leu His Met Gln Ala Leu Pro Pro Arg
545                 550
```

<210> SEQ ID NO 37
<211> LENGTH: 554
<212> TYPE: PRT
<213> ORGANISM: Homo sapiens

<400> SEQUENCE: 37

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Gly Gln Arg Leu Glu Trp Ile
            35                  40                  45

Gly Tyr Phe Ser Pro Gly Asn Asp Asp Phe Lys Tyr Ser Gln Lys Phe
        50                  55                  60

Gln Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Gly Ser Thr Ser Gly Gly Gly Ser Gly Gly Gly Ser Gly
        115                 120                 125

Gly Gly Ser Ser Asp Ile Val Met Ser Gln Ser Pro Asp Ser Leu
    130                 135                 140

Ala Val Ser Leu Gly Glu Arg Val Thr Leu Asn Cys Lys Ser Ser Gln
145                 150                 155                 160

Ser Val Leu Tyr Ser Ser Asn Ser Lys Asn Tyr Leu Ala Trp Tyr Gln
                165                 170                 175

Gln Lys Pro Gly Gln Ser Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Val Gln Ala Glu Asp Val Ala Val
    210                 215                 220

Tyr Tyr Cys Gln Gln Tyr Tyr Ser Tyr Pro Leu Ser Phe Gly Ala Gly
```

```
              225                 230                 235                 240
        Thr Lys Leu Glu Leu Lys Glu Ser Lys Tyr Gly Pro Pro Cys Pro Pro
                            245                 250                 255

Cys Pro Gly Gly Gly Ser Ser Gly Gly Ser Gly Gly Gln Pro Arg
                        260                 265                 270

Glu Pro Gln Val Tyr Thr Leu Pro Pro Ser Gln Glu Met Thr Lys
                        275                 280                 285

Asn Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr Lys
        305                 310                 315                 320

Thr Thr Pro Pro Val Leu Asp Ser Asp Gly Ser Phe Phe Leu Tyr Ser
                            325                 330                 335

Arg Leu Thr Val Asp Lys Ser Arg Trp Gln Glu Gly Asn Val Phe Ser
                        340                 345                 350

Cys Ser Val Met His Glu Ala Leu His Asn His Tyr Thr Gln Lys Ser
                        355                 360                 365

Leu Ser Leu Ser Leu Gly Lys Met Ala Leu Ile Val Leu Gly Gly Val
            370                 375                 380

Ala Gly Leu Leu Leu Phe Ile Gly Leu Gly Ile Phe Phe Lys Arg Gly
        385                 390                 395                 400

Arg Lys Lys Leu Leu Tyr Ile Phe Lys Gln Pro Phe Met Arg Pro Val
                            405                 410                 415

Gln Thr Thr Gln Glu Glu Asp Gly Cys Ser Cys Arg Phe Pro Glu Glu
                        420                 425                 430

Glu Glu Gly Gly Cys Glu Leu Gly Gly Arg Val Lys Phe Ser Arg
                        435                 440                 445

Ser Ala Asp Ala Pro Ala Tyr Gln Gln Gly Gln Asn Gln Leu Tyr Asn
            450                 455                 460

Glu Leu Asn Leu Gly Arg Arg Glu Glu Tyr Asp Val Leu Asp Lys Arg
        465                 470                 475                 480

Arg Gly Arg Asp Pro Glu Met Gly Gly Lys Pro Arg Arg Lys Asn Pro
                            485                 490                 495

Gln Glu Gly Leu Tyr Asn Glu Leu Gln Lys Asp Lys Met Ala Glu Ala
                        500                 505                 510

Tyr Ser Glu Ile Gly Met Lys Gly Glu Arg Arg Arg Gly Lys Gly His
                        515                 520                 525

Asp Gly Leu Tyr Gln Gly Leu Ser Thr Ala Thr Lys Asp Thr Tyr Asp
            530                 535                 540

Ala Leu His Met Gln Ala Leu Pro Pro Arg
        545                 550

<210> SEQ ID NO 38
<211> LENGTH: 554
<212> TYPE: PRT
<213> ORGANISM: Homo sapiens

<400> SEQUENCE: 38

Gln Val Gln Leu Val Gln Ser Gly Ala Glu Val Lys Lys Pro Gly Ala
        1               5                   10                  15

Ser Val Lys Val Ser Cys Lys Ala Ser Gly Tyr Thr Phe Thr Asp His
                        20                  25                  30

Ala Ile His Trp Val Arg Gln Ala Pro Gly Gln Arg Leu Glu Trp Met
                    35                  40                  45
```

```
Gly Tyr Phe Ser Pro Gly Asn Asp Asp Phe Lys Tyr Ser Gln Lys Phe
     50                  55                  60

Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Thr Arg Ser Leu Asn Met Ala Tyr Trp Gly Gln Gly Thr Leu Val Thr
            100                 105                 110

Val Ser Ser Gly Ser Thr Ser Gly Gly Ser Gly Gly Ser Gly
        115                 120                 125

Gly Gly Gly Ser Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Leu Leu Tyr Ser Ser Asn Ser Lys Asn Tyr Leu Ala Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Gln Gln Pro Tyr Ser Tyr Pro Leu Ser Phe Gly Ala Gly
225                 230                 235                 240

Thr Lys Leu Glu Leu Lys Glu Ser Lys Tyr Gly Pro Pro Cys Pro Pro
                245                 250                 255

Cys Pro Gly Gly Gly Ser Ser Gly Gly Gly Ser Gly Gly Gln Pro Arg
            260                 265                 270

Glu Pro Gln Val Tyr Thr Leu Pro Pro Ser Gln Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Arg Leu Thr Val Asp Lys Ser Arg Trp Gln Glu Gly Asn Val Phe Ser
            340                 345                 350

Cys Ser Val Met His Glu Ala Leu His Asn His Tyr Thr Gln Lys Ser
        355                 360                 365

Leu Ser Leu Ser Leu Gly Lys Met Ala Leu Ile Val Leu Gly Gly Val
    370                 375                 380

Ala Gly Leu Leu Leu Phe Ile Gly Leu Gly Ile Phe Phe Lys Arg Gly
385                 390                 395                 400

Arg Lys Lys Leu Leu Tyr Ile Phe Lys Gln Pro Phe Met Arg Pro Val
                405                 410                 415

Gln Thr Thr Gln Glu Glu Asp Gly Cys Ser Cys Arg Phe Pro Glu Glu
            420                 425                 430

Glu Glu Gly Gly Cys Glu Leu Gly Gly Arg Val Lys Phe Ser Arg
        435                 440                 445

Ser Ala Asp Ala Pro Ala Tyr Gln Gln Gly Gln Asn Gln Leu Tyr Asn
450                 455                 460

Glu Leu Asn Leu Gly Arg Arg Glu Glu Tyr Asp Val Leu Asp Lys Arg
```

```
               465                 470                 475                 480
        Arg Gly Arg Asp Pro Glu Met Gly Gly Lys Pro Arg Arg Lys Asn Pro
                            485                 490                 495

Gln Glu Gly Leu Tyr Asn Glu Leu Gln Lys Asp Lys Met Ala Glu Ala
                            500                 505                 510

Tyr Ser Glu Ile Gly Met Lys Gly Glu Arg Arg Arg Gly Lys Gly His
                            515                 520                 525

Asp Gly Leu Tyr Gln Gly Leu Ser Thr Ala Thr Lys Asp Thr Tyr Asp
                            530                 535                 540

Ala Leu His Met Gln Ala Leu Pro Pro Arg
        545                 550
```

<210> SEQ ID NO 39
<211> LENGTH: 119
<212> TYPE: PRT
<213> ORGANISM: Homo sapiens

<400> SEQUENCE: 39

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Gly Ser Thr Ser
        115
```

<210> SEQ ID NO 40
<211> LENGTH: 115
<212> TYPE: PRT
<213> ORGANISM: Homo sapiens

<400> SEQUENCE: 40

```
Ser Ser Asp Ile Val Met Ser Gln Ser Pro Asp Ser Leu Ala Val Ser
1               5                   10                  15

Leu Gly Glu Arg Val Thr Leu Asn Cys Lys Ser Ser Gln Ser Leu Leu
            20                  25                  30

Tyr Ser Gly Asn Gln Lys Asn Tyr Leu Ala Trp Tyr Gln Gln Lys Pro
        35                  40                  45

Gly Gln Ser Pro Lys Leu Leu Ile Tyr Trp Ala Ser Ala Arg Glu Ser
    50                  55                  60

Gly Val Pro Asp Arg Phe Ser Gly Ser Gly Ser Gly Thr Asp Phe Thr
65                  70                  75                  80

Leu Thr Ile Ser Ser Val Gln Ala Glu Asp Val Ala Val Tyr Tyr Cys
                85                  90                  95

Gln Gln Tyr Tyr Ser Tyr Pro Leu Thr Phe Gly Ala Gly Thr Lys Leu
            100                 105                 110

Glu Leu Lys
```

```
115

<210> SEQ ID NO 41
<211> LENGTH: 22
<212> TYPE: PRT
<213> ORGANISM: Homo sapiens

<400> SEQUENCE: 41

Met Leu Leu Leu Val Thr Ser Leu Leu Leu Cys Glu Leu Pro His Pro
1               5                   10                  15

Ala Phe Leu Leu Ile Pro
            20
```